United States Patent [19]
Eggler et al.

[11] Patent Number: 6,166,031
[45] Date of Patent: Dec. 26, 2000

[54] SUBSTITUTED TETRALINS, CHROMANS AND RELATED COMPOUNDS IN THE TREATMENT OF ASTHMA

[75] Inventors: James F. Eggler, Stonington; Anthony Marfat, Mystic; Lawrence S. Melvin, Jr., Ledyard, all of Conn.

[73] Assignee: Pfizer Inc,, New York, N.Y.

[21] Appl. No.: 07/474,734

[22] PCT Filed: Oct. 19, 1987

[86] PCT No.: PCT/US87/02734

§ 371 Date: Apr. 11, 1990

§ 102(e) Date: Apr. 11, 1990

[51] Int. Cl.$^7$ .............. A61K 31/47; A61P 1/14; A61P 11/06; A61P 17/06

[52] U.S. Cl. .......... 514/311; 514/312; 546/152; 546/153; 546/180

[58] Field of Search .............. 546/152–153, 546/180; 514/311, 312

[56] References Cited

U.S. PATENT DOCUMENTS

| | | | |
|---|---|---|---|
| 4,474,788 | 10/1984 | Bantick | 428/258 |
| 4,625,034 | 11/1986 | Neiss et al. | 546/152 |
| 4,631,287 | 12/1986 | Chakraborty et al. | 514/307 |
| 4,661,596 | 4/1987 | Kreft et al. | 546/152 |
| 4,851,409 | 7/1989 | Young et al. | 514/228.2 |
| 4,853,392 | 8/1989 | Cooper et al. | 514/311 |
| 4,923,881 | 5/1990 | Oku et al. | 514/311 |
| 4,965,274 | 10/1990 | Oku et al. | 514/311 |

FOREIGN PATENT DOCUMENTS

| | | |
|---|---|---|
| 056765 | 7/1982 | European Pat. Off. . |
| 206751 | 12/1986 | European Pat. Off. . |
| 0288962 | 11/1988 | European Pat. Off. . |

OTHER PUBLICATIONS

Perrone et al., European Journal of Medicinal Chemistry, vol. 22, 417–19 (1987).

Delgado et al., Canadian Journal of Chemistry, vol. 66, 517–26 (1988).

*Primary Examiner*—Joseph K. McKane
*Assistant Examiner*—Jane C. Oswecki
*Attorney, Agent, or Firm*—Peter C. Richardson; Paul H. Ginsburg; Seth H. Jacobs

[57] ABSTRACT

Substituted tetralins, chromans and related compounds which, by inhibiting 5-lipoxygenase enzyme and/or blocking leukotriene receptors, are useful in the prevention or treatment of asthma, arthritis, psoriasis, ulcers, myocardial infarction and related disease states in mammals; pharmaceutical compositions comprising said compounds; a method of treatment with said compounds; and intermediates useful in the synthesis of said compounds.

12 Claims, No Drawings

SUBSTITUTED TETRALINS, CHROMANS AND RELATED COMPOUNDS IN THE TREATMENT OF ASTHMA

This application is a 371 of PCT/US87/02734 filed Oct. 19, 1987.

BACKGROUND OF THE INVENTION

The present invention is directed to substituted tetralins, chromans and related compounds of the formula (I), depicted below, which by inhibiting 5-lipoxygenase enzyme and/or blocking leukotriene receptors, are useful in the prevention or treatment of asthma, arthritis, psoriasis, ulcers, myocardial infarction and related disease states in mammals. The present invention is also directed to pharmaceutical compositions, a method of treatment and to intermediates useful in the synthesis of said compounds of the formula (I).

Kreft et al., in U.S. Pat. No. 4,661,596, describe compounds which are disubstituted naphthalenes, dihydronaphthalenes or tetralins having the formula

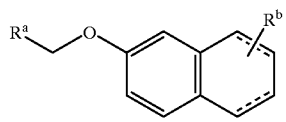

wherein the dotted lines represent optional double bonds, $R^a$ is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and $R^b$ is hydroxy, lower alkoxy, lower alkyl or perfluoro alkyl. Like the compounds of the present invention, these compounds inhibit lipoxygenase enzyme and antagonize the effects of leukotriene D4, and so are useful in the prevention and treatment of asthma.

The chemical nomenclature employed herein generally follows that of "I.U.P.A.C. Nomenclature of Organic Chemistry, 1979 Edition," Pergammon Press, New York, 1979.

SUMMARY OF THE INVENTION

The present invention is directed to racemic or optically active compounds having the structural formula

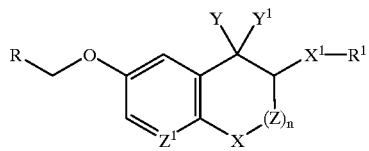

(I)

wherein n is 0 or 1;

X is $CH_2$, O, S, SO, $SO_2$, NH or $N(C_1-C_4)$alkyl;

$X^1$ is $CH_2$, O, S, SO or $SO_2$;

Y and $Y^1$ are taken together and form a carbonyl group, or Y and $Y^1$ are taken separately, Y is hydrogen and $Y^1$ is hydroxy or an acyloxy group which is hydrolyzed to form a hydroxy group under physiological conditions;

Z is $CH_2$, $CHCH_3$, $CH_2CH_2$ or $CH_2CH_2CH_2$;

$Z^1$ is CH or N;

R is 2-, 3- or 4-pyridyl, 2-, 3- or 4-quinolyl, 1-, 3- or 4-isoquinolyl, 3- or 4-pyridazinyl, 3- or 4-cinnolinyl, 1-phthalazinyl, 2- or 4-pyrimidinyl, 2- or 4-quinazolinyl, 2-pyrazinyl, 2-quinoxalinyl, 1-, 2- or 3-indolizinyl, 2-, 4- or 5-oxazolyl, 2-benzoxazolyl, 3-, 4- or 5-isoxazolyl, 5-benzo[c]isoxazolyl, 3-benzo[d] isoxazolyl, 2-, 4- or 5-thiazolyl, 2-benzothiazolyl, 3-, 4- or 5-isothiazolyl, 5-benzo[c]isothiazolyl, 3-benzo[d] isothiazolyl, 1-[$(C_1-C_4)$alkyl]-2-, 4- or 5-imidazolyl, 1-[$(C_1-C_4)$alkyl]-2-benzimidazolyl, 1-[$(C_1-C_4)$alkyl]-3-, 4- or 5-pyrazolyl, 2-[$(C_1-C_4)$alkyl]-3(2H)-indazolyl, or 1-[$(C_1-C_4)$alkyl]-3(1H)-indazolyl; or one of said groups mono- or disubstituted on carbon with the same or different substituents which are bromo, chloro, fluoro, $(C_1-C_4)$alkyl, trifluoromethyl, hydroxy, hydroxymethyl or $(C_1-C_4)$alkoxy, or substituted on adjacent carbons with trimethylene, tetramethylene, $-CH_2-O-CH_2-$ or $-O-CH_2-O-$; and $R^1$ is $(C_1-C_8)$alkyl, $(C_3-C_8)$cycloalkyl, $(C_7-C_{10})$ bicycloalkyl, $(C_4-C_{10})$cycloalkylalkyl, $(C_8-C_{11})$ bicycloalkylalkyl, or one of said groups mono- or disubstituted with the same or different groups which are fluoro, $(C_1-C_4)$alkyl, $(C_1-C_4)$alkoxy, carboxy, [$(C_1-C_4)$alkoxy] carbonyl, or $(C_2-C_5)$alkanoyl;

a pharmaceutically acceptable acid addition salt thereof; or a pharmaceutically acceptable cationic salt when the compound contains a carboxy group.

Because of their ease of preparation and valuable biological activity, the preferred compounds of the formula (I), regardless of the value of Y and $Y^1$, have n as 1, Z as $CH_2$, $Z^1$ as CH, X and $X^1$ each independently as $CH_2$ or O. More preferred compounds further have R as 2-pyridyl or 2-quinolyl and $R^1$ as $(C_2-C_8)$alkyl or $(C_3-C_8)$cycloalkyl. Most preferred are racemic or optically active compounds having the relative stereochemical formula

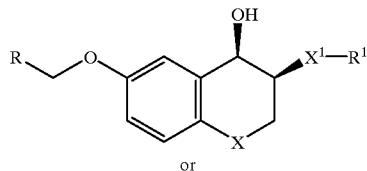

or

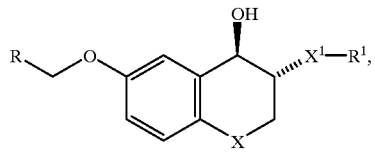

most particularly those racemic or optically active compounds of the formula (II) or (III) wherein X and $X^1$ are each O, R is 2-quinolyl, and $R^1$ is isopropyl or cyclohexyl; or X and $X^1$ are each $CH_2$, R is 2-pyridyl or 2-quinolyl and $R^1$ is n-propyl, as well as the pair of optically active enantiomeric compounds of the formula (III) wherein X and $X^1$ are each $CH_2$, R is 2-quinolyl and $R^1$ is n-propyl.

Said pharmaceutically-acceptable acid addition salts include, but are not limited to, those with HCl, HBr, $HNO_3$, $H_2SO_4$, $H_3PO_4$, methanesulfonic acid, p-toluenesulfonic acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

The reference to $Y^1$ as an acyloxy group which is hydrolyzed to a hydroxy group under physiological conditions refers to esters of a type which are frequently referred to as "pro-drugs." Such esters are now as well-known and common in the medicinal art as pharmaceutically-acceptable salts. Such esters are generally used to enhance oral absorption, but in any event are readily hydrolyzed in vivo to the parent hydroxy compound. The more preferred acyloxy groups are those in which the acyl moiety is the alpha-aminoacyl residue of a naturally occurring L-alpha-amino acid,

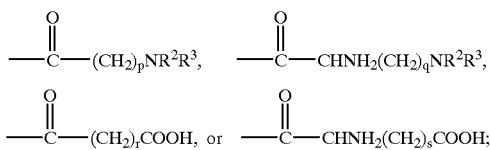

wherein
$R^2$ and $R^3$ are taken separately and are each independently hydrogen or $(C_1-C_4)$alkyl, or $R^2$ and $R^3$ are taken together with the nitrogen to which they are attached to form a pyrrolidine, piperidine, perhydroazepin or morpholine ring;
p is an integer from 1 to 4;
q is an integer from 1 to 3;
r is an integer from 2 to 3; and
s is an integer from 1 to 3.

Also forming a part of the present invention are pharmaceutical compositions for administration to a mammal which comprise a compound of the formula (I) and a pharmaceutically acceptable carrier; and a method of inhibiting 5-lipoxygenase enzyme and/or blocking leukotriene D4 receptors in a mammal, so as to prevent or treat asthma (particularly in man), arthritis, psoriasis, gastrointestinal ulcers, or myocardial infarction.

Finally, the present invention is directed to valuable intermediate compounds having the structural formula

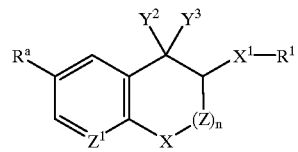

wherein
n, X, Z and $Z^1$ are as defined above;
$Y^2$ and $Y^3$ are taken together and form a carbonyl group, or $Y^2$ and $Y^3$ are taken separately, $Y^2$ is hydrogen and $Y^3$ is hydroxy; and
$R^a$ is hydroxy or benzyloxy.

DETAILED DESCRIPTION OF THE INVENTION

The present invention is readily carried out. Without regard to geometrical (cis-trans) or optical isomers, the compounds of the formula (I) wherein $Y+Y^1$=carbonyl, or Y=H and $Y^1$=OH, and $X^1$=$CH_2$, S or O are prepared according to the chemical transformations which are summarized in Flowsheets 1, 2 and 3, where the symbols n, X, Z, $Z^1$, R and $R^1$ are as defined above. The various transformations found in these flowsheets, as well as transformations required for the preparation of the compounds (I) having other values of Y, $Y^1$ and $X^1$, and methods for separation of cis-trans and optical isomers, are detailed below.

The condensation of Flowsheet 1 is typically carried out with the phenolic group in protected form as shown, methyl being a preferred protecting group only when $X^1$ is $CH_2$. The preferred conditions employ a molar excess of the required aldehyde and a molar excess of a secondary amine such as pyrrolidine or piperidine as base. (It is understood that such a base facilitates the condensation by forming an enamine intermediate.)

Flowsheet 1

When $X^1$ = $CH_2$

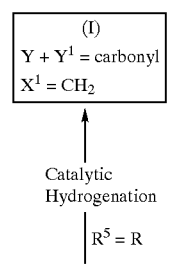

-continued
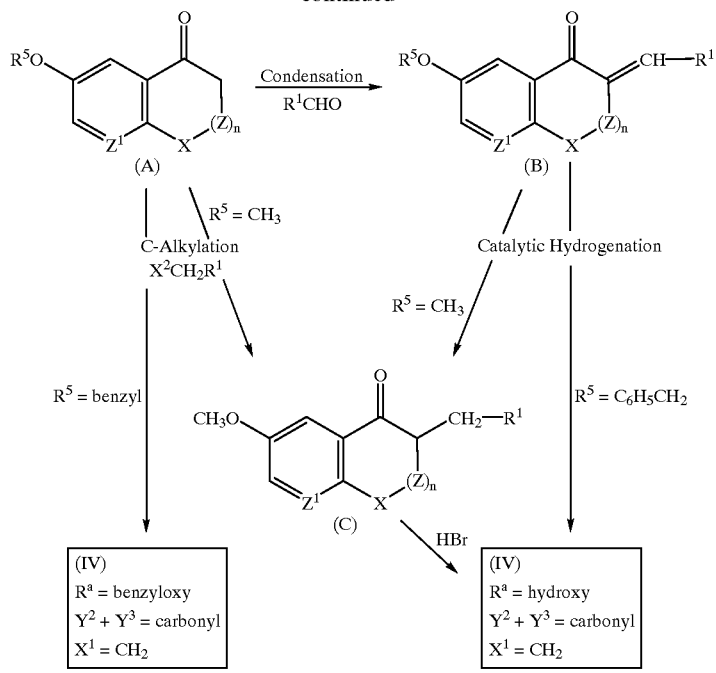
$R^5$ = R, $CH_3$, or $C_6H_5CH_2$
$X^2$ = Nucleophically displaceable group
such as I, Br, Cl, $CH_3SO_3$ or
p-$CH_3C_6H_4SO_3$
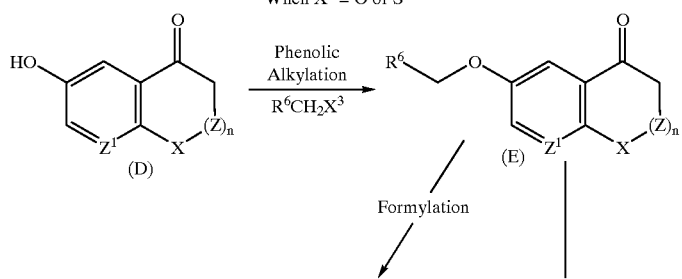

-continued
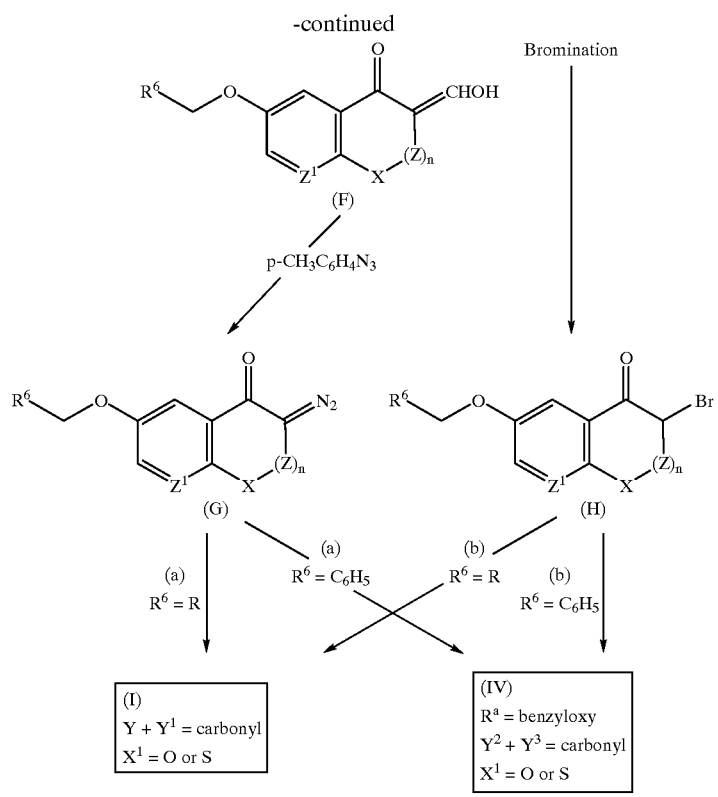
$R^6$ = R or $C_6H_5$
$X^2$ = Cl, Br, I, $CH_3SO_3$, p-$CH_3C_8H_4SO_3$ or other nucleophilically displaceable group
(a) $R^1SH$ or $R^1OH$, rhodium (II) acetate dimer
(b) $R^1SH$ or $R^1OH$, base
Flowsheet 3
When $X^1$ = $CH_2$, O or S
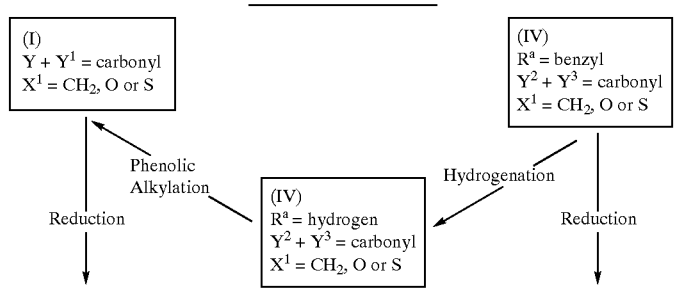

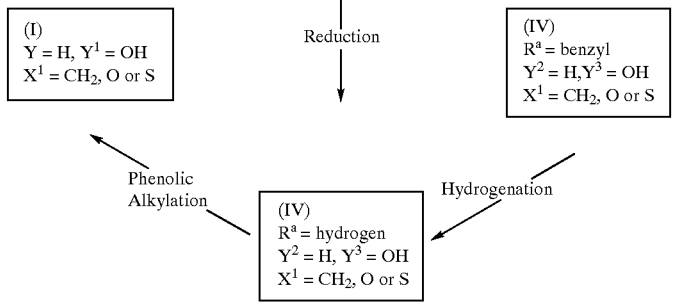

The reaction is generally carried out in a reaction-inert solvent, lower alcohols such as methanol being particularly well suited for this purpose. The temperature conditions for this transformation are not critical, e.g., 0–70° C. is generally satisfactory, with ambient temperature particularly well suited as a matter of convenience.

As used here and elsewhere herein, the expression "reaction-inert solvent" refers to a solvent which does not interact with starting materials, reagents, intermediates or products in a manner which adversely affects the yield of the desired product.

The C-alkylation of Flowsheet 1 is carried out by first converting the ketone (A) to its lithium salt, usually in situ, by the action of substantially one molar equivalent of a strong, sterically hindered base such as lithium diisopropylamide, usually carried out at low temperature (e.g., about −40 to −80° C. conveniently at the temperature of a dry ice-acetone bath). The salt in turn is reacted with the alkylating agent, preferably the highly reactive iodide, usually in molar excess in the presence of a molar excess of hexamethyl phosphoramide, now at higher temperature (e.g., about 0 to 40° C.). Conveniently, the latter reagents are added to the cold lithium salt solution, and the temperature allowed to rise to ambient temperature as the reaction proceeds. The salt preparation and alkylation reaction are usually carried out in the same reaction-inert solvent (e.g., tetrahydrofuran). It will be evident to those skilled in the art that any free hydroxy or carboxy groups in the alkylating reagent should be in protected form (vide supra).

The catalytic hydrogenation transformations (debenzylations, $H_2$-additions to double bond) of Flowsheets 1, 2 and 3 are carried out under conventional conditions, generally in a reaction-inert solvent, and preferably using a noble metal catalyst and moderate conditions of temperature (e.g., about 0 to 70° C.) and hydrogen pressure (e.g., about 1 to 10 atmospheres). While higher pressures may be desirable in selected instances, such moderate pressures permit the use of much less elaborate and expensive equipment. Suitable noble metal catalysts include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be pre-formed or formed in situ by prereduction of an appropriate salt of the catalytic compound. Examples of preferred catalysts are 5% palladium-on-carbon, 5% platinum-on-carbon; 5% rhodium-on-carbon, platinum chloride, palladium chloride, platinum oxide and ruthenium oxide. Most preferred in the present instance is palladium-on-carbon. Solvents generally suitable for the present hydrogenation include lower alkanols, ethyl acetate and tetrahydrofuran.

The methyl ethers [compounds of the formula (C)] in Flowsheet 1 are deblocked to form the corresponding phenol derivative, again, by conventional methods; for example, using of concentrated HBr, or $BBr_3$, both of which are exemplified below.

The phenolic alkylations found in Flowsheets 2 and 3 and the bromine replacement reaction of Flowsheet 2 each represent conventional nucleophilic displacement reactions. These displacements are generally carried out in the presence of a base of sufficient strength to convert the displacing phenol, alcohol or thiol to its salt, and in a quantity at least sufficient to neutralize the by-product acid ($HX^2$, HBr). In those substrates which contain an aliphatic alcohol group [e.g., a compound (IV) wherein $Y^2$ is H and $Y^3$ is OH], bases of sufficient strength to convert that group to the anion will generally be used in an amount no more than sufficient to convert the more acidic phenol to the salt. When either of the reactants contains a group of acidity similar to or greater than that of the nucleophilic displacing compound, such potentially interfering groups are best introduced in protected form (e.g., a heteroaromatic phenolic group as methoxy or benzyloxy, a carboxy group as methyl or benzyl ester, removable by hydrolysis or hydrogenolysis according to methods detailed elsewhere herein). The present nucleophilic displacements are carried out in a reaction-inert solvent, preferably one which is much less acidic than the displacing phenol, alcohol or mercaptan. Most preferred are polar, aprotic solvents such as dimethylformamide or acetone, usually with a molar excess of the more readily available of the two reactants. Temperature is not critical, e.g., about 10–70° C. is usually satisfactory with ambient temperature most convenient. In one preferred variant, the phenol, alcohol or mercaptan is irreversibly converted to the anion with a base such as sodium hydride. Other preferred variants employ $K_2CO_3$ as base in the presence of NaI, or $Cs_2CO_3$ as base in the presence of CsI.

In the special case of X=NH, such nucleophilic displacements will generally be carried out with the NH group protected, e.g., as the N-benzyl derivative (subsequently removed by hydrogenation) or as an N-alkanoyl or N-sulfonyl derivative (subsequently removed under appropriate hydrolysis conditions; for example, the N-tosyl derivative is hydrolyzed by heating in a mixture of acetic acid and concentrated HCl).

The formylation of Flowsheet 2 represents a conventional condensation type reaction of a ketone with an alkyl formate. This reaction is generally in an aprotic reaction-inert solvent such as toluene in the presence of a strong base such as sodium hydride at moderate temperatures (e.g., 0–70° C., conveniently at ambient temperature). The subsequent conversion to the diazo compound is conveniently accomplished with tosyl azide as the reagent, a reaction generally carried out at low temperature (e.g., about −10 to −60° C.) in the presence of molar excess of a tertiary amine (e.g., triethylamine) in a reaction-inert solvent such as $CH_2Cl_2$. In turn, the diazo compound is reacted with an appropriate alcohol or mercaptan in the presence of a catalytic amount of rhodium (II) diacetate dimer to form the desired ether or thioether. The latter transformation is generally carried out in an anhydrous reaction-inert solvent such as toluene at somewhat elevated temperature, e.g., about 50–100° C. Substituent alcohol or carboxy groups which are not intended to react are preferably protected in this transformation, as in the case of the nucleophilic displacement reactions discussed above.

The "reduction" reactions of Flowsheet 3 require the reduction of a ketone to a secondary alcohol, for which a number of selective reagents are available. Where no other $LiAlH_4$ reducible groups (such as carboxy, methoxycarbonyl) are present, that reagent is well suited for this purpose. On the other hand, $NaBH_4$ is preferred as the reducing agent when such reducible groups are present. In either case, these hydride reductions are generally carried out in a reaction-inert solvent (such as tetrahydrofuran in the case of $LiAlH_4$, methanol or a methanol/tetrahydrofuran combination in the case of $NaBH_4$). In either case, temperature is not critical, about 0 to 50° C. being generally satisfactory and ambient temperature preferred. The present reduction step offers the potential of producing a mixture of cis- and trans-isomers [as illustrated in the formulas (II) and (III)] and in the present hydride reduction, that is the result which is generally observed. If one or the other of these isomers is particularly desired, one can usually find a reduction method and set of conditions which will favor the desired isomer. For example, $NaBH_4$ reduction in the presence of cesium chloride will generally strongly favor the cis-isomer. Catalytic hydrogenation is also a generally useful reduction method, generally carried out under conditions which are somewhat more vigorous than those described above (e.g., more prolonged time, higher catalyst level, higher temperature and/or higher pressure). Hydrogenation is preferably carried out on substrates such as

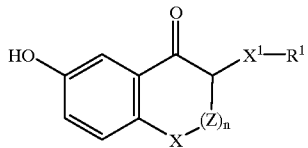

(V)

which contain no other readily hydrogenated group. Pd/C catalyst tends to particularly favor formation of cis-isomer. However, by variation of the catalyst and conditions, it will be possible to modify or even reverse that tendency. Where both cis- and trans-isomers form in the present reduction, they are generally separable by standard chemical methods (e.g., selective or fractional crystallization, chromatography, and so forth).

If compounds wherein $X^1$ is SO or $SO_2$ are desired, they are usually prepared from the corresponding compounds of the formula (I) or (IV) wherein the group $X^1$ as S is already in place. Peroxides are generally used as oxidizing agent. A particularly convenient reagent for this purpose is m-chloroperbenzoic acid. The sulfide is reacted with substantially 1 molar equivalent of this reagent to obtain the sulfoxide and with at least 2 molar equivalents to obtain the sulfone, in a reaction-inert solvent such as $CH_2Cl_2$. Temperature is not critical, e.g., 0–60° C. being generally satisfactory and ambient temperature preferred. However, when X is S, and compounds wherein $X^1$ is SO or $SO_2$ are desired, these are preferably formed by conventional sulfinylation or sulfonylation of an unsubstituted ketone compound of the formula (A), (D) or (E).

Those ketone compounds of the formula (I) or (IV) wherein Y and $Y^1$ or $Y^2$ and $Y^3$ form a carbonyl group contain an asymmetric carbon at the alpha-position which is adjacent to the carbonyl group, and therefore are racemic compounds capable of resolution into optically active enantiomers, e.g., by conversion of the racemate into diastereomeric salts with an optically active acid, which are generally separable by a fractional crystallization process. Alternatively, if the substrate contains a carboxy group, separable diastereomeric salts are formed with an optically active organic amine. Optical activity can also be induced by use of an optically active reagent in the step by which the asymmetric carbon is formed, e.g., use of an optically active Wilkinson type catalyst, or a noble metal supported on an optically active support, in the hydrogenation step. The optically active ketones are also available by conventional reoxidation of an optically active alcohol of the next paragraph, e.g., via the Jones oxidation, which is exemplified below.

The hydroxy compounds of the formula (I) and (IV) wherein Y (or $Y^2$) is hydrogen and $Y^1$ (or $Y^3$) is OH contain two such asymmetric carbons—corresponding to two racemates and four optically active compounds. One of these racemates is the above noted cis-isomer, and the other the trans-isomer. Each of these racemates is capable of resolution into a pair of enantiomers via diastereomeric salts, as detailed in the preceding paragraph. It is preferred, however, to convert the racemic alcohol to corresponding diastereomeric esters or urethanes formed with an optically active acid or isocyanate. Such covalently bonded derivatives are generally subjectable to a broader variety of separation methods (e.g., chromatography) than are diastereomeric salts. Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. A preferred optically active acid in the present case is S-O-acetylmandelic acid. Once the resulting diastereomeric esters are separated, e.g., by chromatographic methods, they are hydrolyzed by conventional methods, e.g., aqueous acid or aqueous base, to obtain the enantiomeric, optically active alcohols.

The prodrug esters of the present invention are prepared by methods similar to those used in the synthesis of esters in the preceding paragraph. Esters with alpha-amino acids, including natural L-amino acids, will generally by prepared from the appropriate amino acid in which the alpha-amino group, substituent $NH_2$ or NH groups (e.g., lysine, ornithine, arginine, histidine, tryptophan), hydroxy groups (serine, homoserine, threonine, tyrosine), mercapto groups (cysteine) and substituent carboxy groups (glutamic acid, aspartic acid) are in protected form (e.g., N-benzyloxycarbonyl, O- and S-benzyl) generally removed by catalytic hydrogenation in a subsequent step. Similarly, in the case of esters with primary or secondary amino substituents, the acids will be coupled with amino groups protected. Such protection is, of course, unnecessary with those acids containing tertiary amino substituents. Finally, the carboxy substituted esters are most conveniently prepared from the cyclic anhydride:

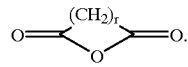

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4 and D4. The first step in this oxidative pathway is the oxidation of arachidonic acid under the influence of 5-lipoxygenase enzyme, an enzyme which is generally inhibited by the compounds (I) of the present invention, thus blocking the synthesis of all leukotrienes. That in itself provides the mechanism sufficient for the utility of the present compounds in the treatment or prevention or asthma (where LTC4 and LTD4 are understood to be mediators), arthritis (where LTB4 is understood to be a mediator in inflammation), psoriasis (where LTB4 is understood to be a mediator), ulcers (where LTC4 and LTD4 are understood to be mediators) and myocardial infarction (where LTB4 is understood to be a mediator). Supplementing this enzyme inhibitory activity is the general ability of the present compounds to antagonize leukotriene D4 (i.e., block LTD4 receptors). In general, the present compounds also antagonize leukotriene B4. For a review concerning leukotrienes, see Bailey et al., *Ann. Reports Med. Chem.* 17, pp. 203–217 (1982).

The in vitro activity of the compounds of the formula (I) is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of 1×10 cells/ml. A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/$H_2O$/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The $IC_{50}$ values are estimated by graphical inspection.

The leukotriene D4 (LTD4) receptor assay tests the ability of a compound to compete with radiolabelled LTD4 for specific LTD4 receptor sites on guinea pig lung membranes. In this test, normal 3–4 week-old guinea pigs are acclimatized under standard conditions for 3 days prior to being sacrificed. Final animal age: 24–31 days. The guinea pigs are stunned by a blow to the back of the neck, and exsanguinated by cutting the carotid artery. The chest cavity is opened and the lungs are removed, rinsed in 50 mM Tris buffer (pH 7.0) and placed in clean buffer. In this and all subsequent operations, all tissue and buffer are kept on ice throughout the preparation, and all centrifugation is carried out at 4° C. Bronchi and connective tissue are trimmed from the lungs. The tissue is weighed and placed in 50 ml polycarbonate tubes with buffer at a ratio of 1 gm tissue/3 ml buffer. The tissue is homogenized by a Tekmar Tissumizer at full speed for 30 seconds and centrifuged in a Sovall SS-34 rotor at 3250 rpm×15 minutes. The supernatant is centrifuged at 19,000 rpm×10 minutes. The resulting pellet is resuspended in buffer with the Tissumizer at medium speed (position 75) for 10 seconds. The resuspension is again centrifuged at 19,000 rpm×10 minutes. The resulting pellet is resuspended by the Tissumizer at slow speed (position 50) for 10 seconds in 1 ml buffer/g of starting tissue. This final suspension is stirred at 4° C. while aliquoted to polypropylene tubes and stored at −70° C. The following are added to a 12×75 mm polystyrene tube:

(1) 25 microL of one of the following:
   A. Dimethylsulfoxide (to determine total binding)
   B. 1 microM LTD4 (to determine non-specific binding)
   C. 30 nanoM—100 microM compound in dimethylsulfoxide
(2) 0.025 ml 3H-LTD4 (specific activity 30–60 Ci/mmol) in 50 mM Tris (pH 7.0)+10 microM L-cysteine (12,000–15,000 cpm/0.025 ml)
(3) 0.2 ml diluted membrane preparation (1 mg/ml) (The preparation is diluted in 50 microM Tris buffer+$MgCl_2$ such that in 200 microL protein, a 10 microM $MgCl_2$ concentration is achieved).

The reaction tubes are incubated at 25° C. for 30 minutes. Four ml of cold Tris buffer+10 microM $MgCl_2$ are added to each tube. The contents are quickly filtered through a Whatman GF/C filter with a Yeda separation device. The filter is washed 3× with 4 ml Tris-$MgCl_2$ buffer. The filter is transferred to a scintillation vial. Ultrafluor scintillation fluid is added. The vial is capped, vortexed and counted for 3 hours. Percent specific binding is calculated using the formula:

$$\%SB=(X-NSB)/(TB-NSB),$$

where
  X=cpm sample
  NSB=cpm non-specific binding
  TB=cpm total binding

Percent specific binding is graphed as a function of compound concentration. $IC_{50}$ is that concentration at which 50% SB occurs. Ki is calculated by using the formula:

$$Ki=(IC_{50})/[1+(L/Kd)],$$

where
  L=concentration of ligand added (microM)=cpm added/cpm of 1 microM 3H-LTD4
  Kd=1 microM (dissociation constant)

Human polymorphonuclear leukocytes are employed to measure the competition of test molecules with [3H]-LTB4 for binding at the LTB4 receptor. In this test neutrophils are isolated from heparinized human peripheral blood (usually 100 ml) using a Hypaque-Ficoll gradient (density 1.095 g/ml). Hanks balanced salt solution (HBSS) containing 0.1 grams/100 ml bovine serum albumin (HBSS-BSA) is used to resuspend the cells. The one step Hypaque-Ficoll technique yields highly pure populations of neutrophils (greater than 95%). Cell viability is assessed by trypan blue dye exclusion (should be greater than 95%), and the functional integrity of the neutrophils was determined by nitroblue tetrazolium reduction (should be greater than 85% positive). Compounds undergoing test are dissolved in dimethylsulfoxide at a concentration of 100 microM. These solutions are diluted by a factor of 500 using HBSS-BSA. A concentration of 100 microM drug is achieved by introducing the diluted sample in a 0.5 ml aliquot into the reaction tube. Serial dilutions of 1-3 and 1-5 are made (as appropriate) and a 0.5 ml aliquot of these dilutions is added to the incubation tube. [3H]-LTB4 (NEN: specific radioactivity, greater than 180 Ci/mmol; 0.005 ml in absolute ethanol) is introduced into borosilicate tubes (12×75 mm). A volume of 0.5 ml of the drug solution (see above) is then added. The binding reaction is initiated by adding 0.5 ml of ice cold neutrophils at a cell density of [$5 \times 10^6$ cells/ml], and continued at 4° C. for 30 minutes. The incubation is terminated by rapid filtration through a Whatman GF/C glass filter to separate the free from the bound radiolabelled ligand. The filters are washed 3-times with 3 ml ice-cold HBSS, dried, placed in 4 ml of Ultrafluor, and counted. Total binding is defined as the CPM present on the filter (cell associated) when radiolabelled ligand is incubated with neutrophils in the absence of any competing agent. Nonspecific binding is obtained by incubating cells with radiolabelled ligand plus 1 microM non-radiolabelled LTB4. Specific binding is total binding CPM corrected for the nonspecific binding CPM. Every tube is corrected for nonspecific binding. Points of half-maximal displacement of radiolabelled ligand are estimated by graphical analysis on a semi-logarithmic plot of percent of specific binding (no competitor present) vs concentration.

To evaluate the compounds of the formula (I) in vivo, they are tested by the so-called PAF lethality assay procedure:
Materials
Mice: CD1 males, all approximately the same weight (approximately 26 grams), 12 per group.
Vehicle for oral drug dosing: EES (5% ethanol, 5% emulphor, 90% saline). Stored at room temperature.
Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.
Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.
Platelet Activating Factor (PAF): A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.
Positive Control: Phenidone is used at 25 mg/kg (its approximate ED 50).
Method
45 minutes before PAF injection, mice are treated orally with drug using 0.1 ml/10 grams body weight. 35 to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.
Variations
1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, arthritis, psoriasis and gastrointestinal ulcers in a mammal, including man, a compound of the formula (I) is given in a 5-lipoxygenase inhibiting and/or leukotriene receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

6-(2-Quinolyl)methoxy-4-chromanone

A mixture of 6-hydroxy-4-chromanone (10.0 g, 0.0609 mol), 2-chloromethylquinoline (11.9 g, 0.0670 mol), sodium iodide (10.0 g, 0.0670 mol), potassium carbonate (25.3 g, 0.183 mol), and acetone (200 ml) was refluxed overnight under $N_2$ atmosphere. After 17 hours the reaction appeared lighter and tlc analysis (10% EtOAc/$CH_2Cl_2$) indicated complete conversion of starting material to a slightly less polar product. The mixture was cooled, filtered, and the filtrate concentrated in vacuo. The residue was taken up in ethyl acetate (400 ml), washed with $H_2O$ and brine, dried over $MgSO_4$, and concentrated in vacuo to a dark brown oil. Purification on a silica gel column eluted with 10% ethyl acetate/$CH_2Cl_2$ gave title product as an off-white solid, 15.3 g (82%), m.p. 112–114° C.; tlc (1:9 ethyl acetate:$CH_2Cl_2$) Rf 0.30.

EXAMPLE 2

3-Hydroxymethylene-6-(2-quinolyl)methoxy-4-chromanone

To a solution of title product of the preceding Example (7.00 g, 0.0229 mol) and excess ethyl formate (35 ml) in toluene (80 ml) at room temperature under argon was added in portions over 5 minutes 2.2 g (0.0458 mol) of 50% sodium hydride in mineral oil. The yellow-green mixture was stirred at room temperature for 5 minutes, followed by the addition of 2 drops of ethanol to initiate the reaction. Within 5 minutes the mixture turned red-orange with gas evolution and was mildly exothermic. The mixture was stirred at room temperature for 1 hour, after which tlc (5% $CH_3OH/CH_2Cl_2$) indicated complete conversion of starting material to a more polar product. The reaction mixture was poured into 400 ml of ice water, adjusted to pH 5 with 2N HCl, and extracted with ethyl acetate (500 ml). The organic layer was washed with $H_2O$ and brine, dried over $MgSO_4$, and concentrated in vacuo to a pasty yellow solid. Repeated trituration with hexanes to remove mineral oil gave present title product in 85% yield, tlc (1:19 $CH_3OH:CH_2Cl_2$) Rf 0.40.

EXAMPLE 3

3-Diazo-6-(2-quinolyl)methoxy-4-chromanone

To a solution of the title product of the preceding Example (7.60 g, 0.023 mol) and dry triethylamine (6.4 ml, 0.046 mol) in dry $CH_2Cl_2$ (100 ml) at −30° C. (dry ice-acetone bath) was added dropwise over 20 minutes a solution of tosyl azide (4.5 g, 0.023 mol) in $CH_2Cl_2$ (25 ml). The reaction mixture was allowed to gradually warm to room temperature overnight with stirring. After 18 hours tlc (20% ethyl acetate/$CH_2Cl_2$) indicated complete disappearance of starting material and formation of a less polar product. The mixture was treated with 1N NaOH (100 ml) and stirred for 10 minutes. After treating with brine, the layers were separated and the organic layer was diluted with 200 ml of ethyl acetate. Methylene chloride was then removed in vacuo. The ethyl acetate residue was washed with $H_2O$ and brine, dried over $MgSO_4$, and concentrated in vacuo to give present title product as a dark yellow solid, 6 g (90%); tlc (1:4 ethyl acetate:$CH_2Cl_2$) Rf 0.27.

EXAMPLE 4

3-Cyclohexyloxy-6-(2-quinolyl)methoxy-4-chromanone

To a suspension of the title product of the preceding Example (1.50 g, 4.53 mmol) and cyclohexanol (1.7 ml, 16.4 mmol) in dry toluene (25 ml) at 70° C. was added 5 mg of rhodium (II) acetate dimer. The reaction quickly evolved $N_2$ and became homogeneous. Tlc analysis (20% ethyl acetate/$CH_2Cl_2$) indicated formation of a less polar product and only a trace of starting material. The reaction mixture was concentrated in vacuo. The residue was taken up in ethyl acetate (100 ml), washed with $H_2O$ and brine, dried over $MgSO_4$, and concentrated in vacuo to an amber oil. Silica gel column chromatography, eluting with 10% ethyl acetate/$CH_2Cl_2$, gave the desired product as a yellow residue, 0.59 g (32%); tlc (1:4 ethyl acetate:$CH_2Cl_2$) Rf 0.68. IR (KBr) 2940, 1700, 1490 $cm^{-1}$. MS (m/e) 403.1780 ($M^+$).

By substituting octyl mercaptan for the cyclohexanol, this process is used to prepare 3-octylthio-6-(2-quinolyl) methoxy-4-chromanone.

EXAMPLE 5 cis- and trans-3-Cyclohexyloxy-6-(2-quinolyl) methoxy-4-chromanol

To a solution of the title product of the preceding Example (580 mg, 1.44 mmol) in methanol (30 ml) at 0–5° C. was added 56 mg (1.45 mmol) of sodium borohydride. The reaction mixture was allowed to warm to room temperature with stirring. After 1 hour, tlc (20% ethyl acetate/$CH_2Cl_2$) indicated complete conversion of starting material to two more polar products. The mixture was concentrated in vacuo. The residue was taken up in ethyl acetate, washed with $H_2O$ and brine, dried over $MgSO_4$, and concentrated in vacuo to a yellow-white solid. Silica gel column chromatography eluting with 20% ethyl acetate/$CH_2Cl_2$ afforded less polas cis-title product as a yellow foam (450 mg) and more polar trans-title product as a light yellow oil (30 mg). Total yield=82%. The cis-isomer was recrystallized from toluene-hexanes to give 417 mg of yellow-white needles, m.p. 127–130° C., and the trans-isomer was triturated with hexanes to give 11 mg of a white solid, m.p. 63–65° C.

cis-isomer. IR (KBr) 1500, 2940 $cm^{-1}$. MS (m/e) 405.1922 ($M^+$). Analysis calculated for $C_{25}H_{27}NO_4$: C, 74.05; H, 6.71; N, 3.45%. Found: C, 74.07; H, 6.69; N, 3.38%.

trans-isomer. IR (KBr) 1495, 2940 $cm^{-1}$. MS (m/e) 405.1980 ($M^+$).

By the same method, the 3-octylthio analog of the preceding Example is converted to a mixture of cis- and trans-3-octylthio-6-(2-quinolyl)methoxy-4-chromanol.

EXAMPLE 6

3-(1-Methylethoxy)-6-(2-quinolyl)methoxy-4-chromanone

By the methods of Example 4, title product of Example 3 (1.12 g) and isopropyl alcohol were converted to present chromatographed title product, 1.48 g (81%), m.p. 85° C.; tlc (1:9 ethyl acetate:$CH_2Cl_2$) Rf 0.35.

EXAMPLE 7 cis- and trans-3-(1-Methylethoxy)-6-(2-quinolyl) methoxy-4-chromanol

By the methods of Example 5, title product of the preceding Example (1.38 g) was converted to present chromatographed title products.

cis-isomer. 1.19 g (86%), m.p. 116–118° C., less polar. IR (KBr) 1490 $cm^{-1}$. MS (m/e) 365.1360 ($M^+$)

Analysis calculated for $C_{22}H_{23}NO_4$: C, 72.31; H, 6.34; N, 3.83%. Found: C, 71.95; H, 6.01; N, 3.76%.

trans-isomer. 0.09 g, m.p. 102–103° C., more polar. IR (KBr) 1500 $cm^{-1}$. MS (m/e) 365.1360 ($M^+$)

EXAMPLE 8

2-Butyl-3,4-dihydro-7-methoxy-1(2H)-naphthalenone

To a −78° C. solution of lithium diisopropyl amide [from 4.37 ml (31.2 mmol) of diisopropyl amine in 28 ml tetrahydrofuran and 11.9 ml (29.8 mmol) of 2.5M n-butyllithium] was slowly added (over 15 minutes) a solution of 5.00 g (28.4 mmol) of 3,4-dihydro-7-methoxy-1(2H)-naphthalenone in 10 ml tetrahydrofuran. The resulting reaction mixture was stirred 10 minutes at −78° C. The cooling bath was then changed to a 0° C. ice-water bath, and was immediately followed by the rapid addition of 3.98 ml (35 mmol) of n-butyl iodide. Hexamethylphosphoramide (10.4 ml, 60 mmol) was then added and the resultant solution atirred at 25° C. for 2 hours. The reaction was added to a mixture of 200 ml saturated ammonium chloride and 300 ml ether. The organic layer was separated, washed with saturated ammonium chloride (200 ml), saturated sodium chloride (200 ml), dried over magnesium sulfate and evaporated to an oil, which was purified via column chromatography on 250 g of silica gel eluted with 5% ether-hexane to give 1.6 g (24%) of present title product as an oil.

$^1$H-NMR(CDCl$_3$)delta(ppm): 0.92 (bt, CH$_3$), 1.1–2.7 (m, 9H), 2.87 (m, CH$_2$), 3.80 (OCH$_3$), 7.0 (m, 2ArH) and 7.41 (d, J=2 Hz, ArH).

EXAMPLE 9

2-Butyl-3,4-dihydro-7-hydroxy-1(2H)-naphthalenone

A mixture of 19.1 g (82.4 mmol) of title product of the preceding Example in 77 ml glacial acetic acid and 77 ml concentrated hydrobromic acid was heated at reflux for 3 hours while collecting a small (about 30 ml) distillate. The reaction was cooled, added to 1 liter ice-cold water and extracted with three 200 ml portions of ether. The combined ether extracts were washed with 1 liter water and 500 ml saturated sodium bicarbonate, dried over magnesium sulfate and evaporated to an oil that solidified on standing to give 17.2 g (96%) of present title product, recrystallized from cold ether-hexane, m.p. 55–58° C. IR (CHCl$_3$) 3352, 3580, 1671 cm$^{-1}$.

$^1$H-NMR(CDCl$_3$)delta(ppm): 0.90 (m, CH$_3$), 1.1–2.7 (m, 9H), 2.90 (m, CH$_2$), 7.1 (m, 2ArH) and 7.75 (bs, 1ArH).

Analysis calculated for C$_{14}$H$_{18}$O$_2$: C, 77.03; H, 8.31% Found: C, 77.25; H, 8.25%.

EXAMPLE 10

2-Butyl-3,4-dihydro-7-(2-quinolyl)methoxy-1(2H)-naphthalenone

A mixture of 4.35 g (20.0 mmol) of title product of the preceding Example, 4.27 g (20.0 mmol) of 2-chloromethylquinoline hydrochloride, 16.3 g (50 mmol) of cesium carbonate and 200 mg (0.769 mmol) of cesium iodide in 43 ml of acetone was heated at reflux for 21 hours. The reaction was cooled, diluted with 43 ml ether and filtered. The filtrate was evaporated to an oil which was purified via column chromatography on 120 g of silica gel eluted with dichloromethane to give present title product as an oil (5.55 g). This purified oil was crystallized by trituration with hexane to give 3.22 g (45%) of crystalline product, m.p. 49–51° C.

MS (m/e) 359 (M$^+$), 303, 142 and 115. IR(CHCl$_3$) 1670, 1600, 1568 cm$^{-1}$.

$^1$H-NMR(CDCl$_3$)delta(ppm): 0.90 (m, CH$_3$), 1.1–2.7 (m, 9H), 2.85 (m, CH$_2$), 5.34 (s, OCH$_2$) and 7.1–8.2 (m, 9ArH).

Analysis calculated for C$_{24}$H$_{25}$NO$_2$: C, 80.18; H, 7.01; N, 3.90% Found: C, 80.44; H, 7.08; N, 3.76%.

EXAMPLE 11 cis- and trans-2-Butyl-1,2,3,4-tetrahydro-7-(2-quinolyl)methoxy-1-naphthol

To a 0° solution of 2.00 g (5.57 mmol) of the title product of the preceding Example in 40 ml methanol was added 1.26 g sodium borohydride. The reaction was stirred 2 hours at 0° C. and then concentrated on a rotating evaporator. The residue was dissolved in a mixture of ether and saturated NaCl. The organic layer was dried over magnesium sulfate and evaporated to an oil, which was purified via medium pressure liquid chromatography on silica gel eluting with 1:3 ether:toluene to give, in sequence of elution, 1.0 g (50%) of the cis-isomer and 770 mg (38%) of the trans-isomer, both as oils. Both isomers were crystallized from ether/hexane.

cis-isomer. m.p. 78.5–80° C. MS (m/e) 361 (M$^+$) 342, 286, 143, 142 and 115. IR (CHCl$_3$) 3590, 3400, 1609, 1600, 1572 cm$^{-1}$.

$^1$H-NMR(CDCl$_3$, 300 MHz)delta(ppm): 0.89 (t, J=7 Hz, CH$_3$), 1.2–1.7 (m, 9H), 2.55–2.82 (m, CH$_2$), 4.53 (d, J=4.0 Hz, CH), 4.73 (OH), 5.33 (s, CH$_2$O), 6.85 (dd, J=8, 2 Hz, ArH), 6.98 (m, 2ArH), 7.49 (dd, J=8, 8 Hz, ArH), 7.62 (d, J=8 Hz, ArH), 7.68 (dd, J=8, 8 Hz, ArH), 7.77 (d, J=8 Hz, ArH), 8.03 (d, J=8 Hz, ArH) and 8.13 (d, J=8 Hz, ArH).

Analysis calculated for C$_{24}$H$_{27}$NO$_2$: C, 79.74; H, 7.53; N, 3.87%. Found: C, 79.44; H, 7.42; N, 3.81%.

trans-isomer: m.p. 70–72° C. MS (m/e) 361 (M$^+$) 286, 143, 142 and 115. IR (CHCl$_3$) 3580, 3435, 1605, 1600, 1575 cm$^{-1}$.

$^1$H-NMR(CDCl$_3$, 300 MHz)delta(ppm): 0.87 (t, J=8 Hz, CH$_3$), 1.1–1.8 (m, 8H), 1.97 (m, 1H), 2.66 (m, CH$_2$), 4.32 (t, J=6.98 Hz, CH), 5.33 (s, OCH$_2$), 6.83 (dd, J=8, 2 Hz, ArH), 6.96 (d, J=8 Hz, ArH), 7.15 (d, J=2 Hz, ArH), 7.49 (dd, J=8, 8 Hz, ArH), 7.63 (d, J=8 Hz, ArH), 7.66 (dd, J=8, 8 Hz, ArH), 7.77 (d, J=8 Hz, ArH), 8.03 (d, J=8 Hz, ArH) and 8.13 (d, J=8 Hz, ArH).

Analysis calculated for C$_{24}$H$_{27}$NO$_2$: C, 79.74; H, 7.53; N, 3.87%. Found: C, 79.38; H, 7.42; N, 3.79%.

EXAMPLE 12

Diastereomeric trans-2-Butyl-1,2,3,4-tetrahydro-7-(2-quinolyl)methoxy-1-naphthyl R-O-acetylmandelates To a 0° solution of 764 mg (2.12 mmol) of the trans-title product of the preceding Example, 493 mg (2.54 mmol) (R)-(–)-O-acetylmandelic acid and 305 mg (2.5 mmol) of 4-(N,N-dimethylamino)pyridine in 4 ml dichloromethane was added 480 mg (2.32 mmol) of dicyclohexylcarbodiimide. After 5 minutes, the reaction was allowed to warm and was stirred at 25° C. for 3 hours. The precipitate formed was removed by filtration and the filtrate evaporated to an oil, which was purified via medium pressure liquid chromatography on silica gel eluted with 25–50% ether-hexane to yield in sequence elution diastereomeric title products A and B. Each was crystallized from ether-hexane to give 436 mg (39%) of diastereomer A and 466 mg (41%) of diastereomer B.

Diastereomer A. m.p. 93–94° C. $^1$H-NMR(CDCl$_3$, 300 MHz)delta(ppm): 0.86 (t, J=7 Hz, CH$_3$), 1.1–2.1 (m, 9H), 2.18 (s, CH$_3$CO), 2.66 (m, CH$_2$), 4.98 (AB pattern, OCH$_2$), 5.75 (d, J=6 Hz, CH), 5.88 (s, CH), 6.34 (d, J=2 Hz, ArH), 6.77 (dd, J=8, 2 Hz, ArH), 6.93 (d, J=8 Hz, ArH), 7.1–7.6 (m, 7ArH), 7.71 (dd, J=8, 8 Hz, ArH), 7.81 (d, J=8 Hz, ArH), 8.07 (d, J=8 Hz, ArH) and 8.16 (d, J=8 Hz, ArH).

Diastereomer B. m.p. 70–81° C. $^1$H-NMR(CDCl$_3$, 300 MHz)delta(ppm): 0.72 (t, J=7 Hz, CH$_3$), 0.8–1.9 (m, 9H), 2.18 (s, CH$_3$CO), 2.63 (m, CH$_2$), 5.31 (AB pattern, OCH$_2$), 5.77 (d, J=6 Hz, CH), 5.87 (s, CH), 6.85 (dd, J=8, 2 Hz, ArH), 6.93 (d, J=2 Hz, ArH), 6.95 (d, J=8 Hz, ArH), 7.3 (m, 2ArH), 7.45 (m, 2ArH), 7.67 (m, 2ArH), 7.79 (d, J=8 Hz, ArH), 8.05 (d, J=8 Hz, ArH), and 8.15 (d, J=8 Hz, ArH).

EXAMPLE 13

(−)-trans-2-Butyl-1,2,3,4-tetrahydro-7-(2-quinolyl)methoxy-1-naphthol

A mixture of 405 mg (0.75 mmol) of diastereomer A of the preceding Example and 832 mg (6.03 mmol) of anhydrous potassium carbonate in 6.25 ml methanol, 6.25 ml tetrahydrofuran and 1.5 ml water was stirred 15 hours at 25° C. The reaction was then added to 100 ml saturated sodium chloride and extracted with three 30 ml portions of ether. The combined ether extracts were dried over magnesium sulfate and evaporated to an oil. This oil was crystallized from ether-hexane to give 160 mg (59%) of present title product, m.p. 59–61° C.

$[alpha]_D^{20}$=−26.3° ($CH_3OH$, c=0.001). $^1$H-NMR($CDCl_3$, 300 MHz)delta(ppm): 0.89 (t, J=7 Hz, $CH_3$), 1.1–2.1 (m, 9H), 2.68 (m, $CH_2$), 4.33 (dd, J=6, 6 Hz, CH), 5.36 (s, $OCH_2$), 6.83 (dd, J=8, 2 Hz, ArH), 6.97 (d, J=8 Hz, ArH), 7.17 (d, J=2 Hz, ArH), 7.50 (dd, J=8, 8 Hz, ArH), 7.65 (d, J=8 Hz, ArH), 7.69 (dd, J=8, 8 Hz, ArH), 7.79 (d, J=8 Hz, ArH), 8.04 (d, J=8 Hz, ArH) and 8.15 (d, J=8 Hz, ArH).

EXAMPLE 14

(+)-trans-2-Butyl-1,2,3,4-tetrahydro-7-(2-quinolyl)methoxy-1-naphthol

By the methods of the preceding Example, diastereomer B product of Example 13 (0.46 g) was converted to present crystallized title product, 0.13 g (54%), m.p. 58–59° C.

$[alpha]_D^{20}$=+23.6° ($CH_3OH$, c=0.001). $^1$H-NMR identical to that of the (−)-isomer of the preceding Example.

EXAMPLE 15

2-Butyl-3,4-dihydro-7-(2-pyridyl)methoxy-1 (2H)-naphthalenone

By the method of Example 10, the title product of Example 9 (5.70 g, 34.3 mmol) and 2-picolyl chloride hydrochloride (5.63 g, 34.3 mmol) were converted to present title product, 4.37 g (41%), m.p. 56–60° C.

MS (m/e) 309 ($M^+$), 253, 93 and 92. IR ($CHCl_3$) 1677, 1608, 1594, 1573 $cm^{-1}$. $^1$H-NMR($CDCl_3$)delta(ppm): 0.98 (m, $CH_3$), 1.1–2.7 (m, 9H), 2.96 (m, $CH_2$), 5.25 (s, $CH_2O$), 7.05–7.9 (m, 6 ArH) and 8.3 (bd, J=6 Hz, ArH).

Analysis calculated for $C_{20}H_{23}NO_2$: C, 77.64; H, 7.49; N, 4.35%. Found: C, 77.93; H, 7.42; N, 4.50%.

EXAMPLE 16 cis- and trans-2-Butyl-1,2,3,4-tetrahydro-7-(2-pyridyl)methoxy-1-naphthol

By the methods of Example 11, the title product of the preceding Example (2.29 g, 7.41 mmol) was converted to present title products.

cis-isomer. 0.96 g (42%), m.p. 101–103° C.; less polar. MS (m/e) 311 ($M^+$), 236, 199, 94, 93 and 92. IR ($CHCl_3$) 3592, 3437, 1610, 1594, 1574 $cm^{-1}$. $^1$H-NMR($CDCl_3$, 300 MHz)delta(ppm): 0.87 (m, $CH_3$), 1.1–1.9 (m, 9H), 2.5–2.8 (m, $CH_2$), 4.51 (bs, CH), 5.13 (s, $CH_2O$), 6.80 (d, J=8 Hz, ArH), 6.91 (bs, ArH), 6.97 (bd, J=8 Hz, ArH), 7.14 (dd, J=8, 8 Hz, ArH), 7.44 (d, J=8 Hz, ArH), 7.63 (dd, J=8, 8 Hz, ArH) and 8.51 (d, J=5 Hz, ArH).

Analysis calculated for $C_{20}H_{25}NO_2$: C, 77.14; H, 8.09; N, 4.50%. Found: C, 77.31; H, 7.94; N, 4.46%.

trans-isomer. 1.12 g (49%), m.p. 62–64° C.; more polar. MS (m/e) 311 ($M^+$), 292, 236, 199, 94, 93 and 92. IR ($CHCl_3$) 3584, 3414, 1609, 1594, 1574 $cm^{-1}$. $^1$H-NMR ($CDCl_3$, 300 MHz)delta(ppm): 0.89 (m, $CH_3$), 1.1–2.1 (m, 9H), 2.67 (m, $CH_2$), 4.32 (bs, CH), 5.15 (s, $OCH_2$), 6.79 (dd J=8, 2 Hz, ArH), 6.96 (d, J=8 Hz, ArH), 7.11 (d, J=2 Hz, ArH), 7.17 (dd, J=8, 8 Hz, ArH), 7.48 (d, J=8 Hz, ArH), 7.66 (dd, J=8, 8 Hz, ArH) and 8.53 (d, J=5 Hz, ArH).

EXAMPLE 17

3-Isopropyl-6-benzyloxy-4-chromanone

By the method of Example 8, 6-benzyloxy-4-chromanone and isopropyl iodide are converted to present title product.

EXAMPLE 18

3-Isopropyl-6-hydroxy-4-chromanone

The title product of the preceding Example (10 g) is hydrogenated at 44 psig in the presence of 1 g of 5% Pd/C at room temperature in 200 ml of $CH_3OH$ and 100 ml of tetrahydrofuran until substantially one molar equivalent of $H_2$ has been taken up. The catalyst is recovered by filtration over diatomaceous earth and present title product recovered by evaporating the filtrate to dryness.

EXAMPLE 19

3-Isopropyl-6-(2-quinolyl)methoxy-4-chromanone

By the method of Example 1, the product of the preceding Example is converted to present title product.

EXAMPLE 20 cis- and trans-3-Isopropyl-6-(2-quinolyl)methoxy-4-chromanol

By the method of Example 5, the product of the preceding Example is converted to present title product.

EXAMPLE 21

By the method of Example 1 or of Example 10, substituting the appropriate chloromethyl substituted heterocycle for 2-chloromethylquinoline, the title product of Example 9 is converted to the following additional products:

2-Butyl-3,4-dihydro-7-(3-pyridyl)methoxy-1 (2H)-naphthalenone;
2-Butyl-3,4-dihydro-7-(4-pyridyl)methoxy-1 (2H)-naphthalenone;
2-Butyl-3,4-dihydro-7-(2-pyrazinyl)methoxy-1 (2H)-naphthalenone;
2-Butyl-3,4-dihydro-7-(6-fluoro-2-quinolyl)methoxy-1 (2H)-naphthalenone;
2-Butyl-3,4-dihydro-7-(2-benzthiazolyl)methoxy-1 (2H)-naphthalenone;
2-Butyl-3,4-dihydro-7-(2-pyrimidinyl)methoxy-1 (2H)-naphthalenone; and
2-Butyl-3,4-dihydro-7-(2-quinazolinyl)methoxy-1 (2H)-naphthalenone;

By the method of Example 11, these compounds are converted to the corresponding cis- and trans-2-butyl-1,2,3,4-tetrahydro-7-(substituted)methoxy-1-naphthol.

EXAMPLE 22

3-Pentylidene-6-(2-quinolyl)methoxy-4-chromanone

To a 25° C. mixture of 0.112 mol of the title product of Example 1 and 0.169 mol of pentanal in 100 ml of methanol is added 14.1 ml (0.169 mol) of pyrrolidine. The resultant solution is allowed to stir 60 hours at 25° C., cooled to 0° C. and filtered to yield of the title compound.

Substitution of the appropriate aldehyde for pentanal in this process produces:

3-(2-Cyclopentylethylidene)-6-(2-quinolyl)methoxy-4-chromanone;
3-(2-Ethoxypropylidene)-6-(2-quinolyl)methoxy-4-chromanone; and
3-(4-Methoxycarbonyl)butylidene)-6-(2-quinolyl)-methoxy-4-chromanone.

EXAMPLE 23

3-Pentyl-6-(2-quinolyl)methoxy-4-chromanone

A mixture of 25.2 g of the title product of the preceding Example and 2 g of 5% Pd/C/50% $H_2O$ in 1 liter ethyl acetate is hydrogenated at 35 psig hydrogen until there is uptake of substantially 1 molar equivalent of $H_2$ (about 18 hours). The reaction is filtered through diatomaceous earth with ethyl acetate wash, and the combined filtrate and wash evaporated to dryness to yield title product.

By the same method, the other products of the preceding Example are converted to:

3-(2-Cyclopentylethyl)-6-(2-quinolyl)methoxy-4-chromanone;
3-(3-Ethoxypropyl)-6-(2-quinolyl)methoxy-4-chromanone; and
3-(4-Methoxycarbonyl)butyl-6-(2-quinolyl)methoxy-4-chromanone.

By the method of Example 11, the products of this Example are further converted to the corresponding cis- and trans-2-(substituted)-6-(2-quinolyl)methoxy-4-chromanols.

EXAMPLE 24

3-(4-Carboxybutyl)-6-(2-quinolyl)-methoxy-4-chromanone

To a solution of 630 mg of the 4-(methoxycarbonyl)butyl substituted product of the preceding Example in 100 ml methanol and 25 ml tetrahydrofuran is added 10 ml of 5N NaOH. The reaction is heated on a steam bath for 10 minutes. The volatiles are evaporated in vacuo, and the residue dissolved in water and acidified to pH 5 with dilute HCl. The precipitated title product is collected by filtration and allowed to air-dry.

EXAMPLE 25 cis-3-(4-Carboxybutyl)-6-(2-quinolyl)methoxy-4-chromanol

By the hydrogenation method of Example 18, but with twice the catalyst level and a temperature of 40° C., again with uptake of substantially 1 molar equivalent of $H_2$, the title product of the preceding Example is converted primarily to present title product.

EXAMPLE 26

7-Benzyloxy-3,4-dihydro-4-(cyclopentyl)methoxy-1-benzoxepin-5 (2H)-one

To a solution of 1.5 g of (cyclopentyl)methanol in 50 ml of tetrahydrofuran is added 720 mg of 50% sodium hydride. After stirring until evolution of $H_2$ is substantially complete (about 30 minutes), a solution of 4.5 g of crude 7-benzyloxy-4-bromo-3,4-dihydro-1-benzoxepin-5 (2H)-one is added. The reaction is allowed to stir at room temperature for 5 hours. The tetrahydrofuran is evaporated in vacuo, and the residue dissolved in ethyl acetate and washed with water. The ethyl acetate layer is dried over sodium sulfate and evaporated in vacuo to yield present title product.

EXAMPLE 27

3,4-Dihydro-7-hydroxy-4-(cyclopentyl)methoxy-1-benzoxepin-5 (2H)-one

A mixture of 2 g of the product of the preceding Example, 200 mg of 10% Pd/C and 50 ml of methanol is hydrogenated in a Parr shaker at 50 psig for 2.5 hours. The catalyst is removed by filtration and the filtrate evaporated in vacuo to yield present title product which is used without purification in the next step.

EXAMPLE 28 cis and trans-2,3,4,5-Tetrahydro-4-(cyclopentyl)methoxy-1-benzoxepin-5,7-diol

To a solution of 3.5 g of the product of the preceding Example in 100 ml of tetrahydrofuran is added 1 g of lithium aluminum hydride. The reaction is allowed to stir at room temperature for 15 minutes, then quenched with water, acidified to pH 4 with dilute hydrochloric acid and extracted with ethyl acetate. The ethyl acetate layer is dried over sodium sulfate and evaporated in vacuo to yield the product mixture, which is separated by column chromatography on silica gel eluting with dichloromethane/ether.

EXAMPLE 29

(+)-trans-2,3,4,5,-Tetrahydro-4-(cyclopentyl)methoxy-7-(2-quinolyl)methoxy-1-benzoxepin-5-ol To a solution of 840 mg of the trans-title product of the preceding Example in 25 ml of dimethylformamide is added 154 mg of 50% NaH. After stirring for 20 minutes, 570 mg of 2-chloromethylquinoline is added. The reaction is stirred at room temperature for 1 hour, poured into water and extracted with ethyl acetate. The ethyl acetate layer is dried over sodium sulfate and evaporated in vacuo to afford present title The corresponding cis-product is prepared in like manner.

EXAMPLE 30

3-(Octylsulfinyl)-6-(2-quinolyl)methoxy-4-chromanone

To a solution of the 3-(octylthio) product of Example 4 (0.57 mmol) in $CH_2Cl_2$ (25 ml) at 0° C. is added 125 mg (0.57 mmol) of m-chloroperbenzoic acid. The reaction is stirred at 0° C. for 2 hours, then diluted with $CH_2Cl_2$ (50–70 ml), washed with saturated $NaHCO_3$, $H_2O$ and brine, dried over $Na_2SO_4$, and concentrated in vacuo to yield present title product.

EXAMPLE 31

3-(Octanesulfonyl)-6-(2-quinolyl)methoxy-4-chromanone

To a partial solution of the 3-(octylthio) product of Example 4 (1.20 mmol) in 50 ml of hot methanol is added a solution of KHSO$_3$ (2.20 g, 3.58 mmol) in H$_2$O (20 ml). The reaction is stirred at room temperature for 30 minutes, then diluted with H$_2$O (200 ml) and ethyl acetate (250 ml). The organic layer is washed 2×H$_2$O and brine, dried over Na$_2$SO$_4$, and stripped to dryness to yield title product.

EXAMPLE 32

7,8-Dihydro-7-methyl-3-(2-quinolyl)methoxy-5 (6H)-quinolone

By the method of Example 1, 7,8-dihydro-3-hydroxy-7-methyl-5 (6H)-quinolone and 2-chloromethylquinoline were converted to present title product in 67% yield, m.p. 141–144° C.

MS (m/e) calculated: 318.1365; found: 318.1325.

EXAMPLE 33

6-Butyl-7,8-dihydro-7-methyl-3-(2-quinolyl) methoxy-5 (6H)-quinolone

By the method of Example 8, the title product of the preceding Example is converted to present title product.

EXAMPLE 34 cis- and trans-6-Butyl-7,8-dihydro-7-methyl-3-(2-quinolyl)methoxy-5 (6H)-quinolone By the method of Example 2, the title product of the preceding Example is converted to a mixture of present title products. It is believed that this product is a mixture of 6,7-cis and 6,7-trans-isomers, although the possibility that the product comprises substantially one or the other of these isomers is not excluded.

EXAMPLE 35 c-6-Butyl-5,6,7,8-tetrahydro-c- and t-7-methyl-3-(2-quinolyl)methoxy-r-5-quinolol and t-6-Butyl-5,6,7, 8-tetrahydro-c- and t-7-methyl-3-(2-quinolyl) methoxy-r-5-quinolol By the method of Example 5, the product of the preceding Example is converted to present title products named according to the *IUPAC Nomenclature of Organic Chemistry*, 1979 Ed., pp. 477–8. Each of these products is believed to be a mixture of two compounds, one having the 7-methyl group cis(c) relative(r) to the 5-hydroxy group and the other having the 7-methyl group trans(t) relative(r) to the 5-hydroxy group. However, the possibility that each of these products comprises substantially one or the other of these c-7 or t-7 isomers is not excluded.

EXAMPLE 36

6 (8H)-Hydroxymethylene-7-methyl-3-(2-quinolyl) methoxy-5 (7H)-quinolone

By the method of Example 2, the title product of Example 61 was converted to present title product in 99% yield; tlc (19:1 CH$_2$Cl$_2$:ethanol) Rf 0.6.

EXAMPLE 37

6 (8H)-Diazo-7-methyl-3-(2-quinolyl)methoxy-5 (7H)-quinolone

By the method of Example 3, the title product of the preceding Example was converted to present title product in 99% yield; tlc (19:1 CH$_2$Cl$_2$:ethanol) Rf 0.25.

EXAMPLE 38 cis- and trans-7,8-Dihydro-7-methyl-6-pentoxy-3-(2-quinolyl)methoxy-5 (6H)-quinolone (See Example 34 for comment re isomer composition.)

By the method of Example 4, the title product of the preceding Example and pentanol are converted to a mixture of present title products.

EXAMPLE 39

5,6,7,8-Tetrahydro-c- and t-7-methyl-c-6-phenoxy-3-(2-quinolyl)methoxy-r-5-quinolyl and 5,6,7,8-Tetrahydro-c- and t-7-methyl-t-6-phenoxy-3-(2-quinolyl)methoxy-r-5-quinolyl (See Example 35 for comments re nomenclature and isomer composition.)

By the method of Example 5, the title products of the preceding Example are converted to present title products.

EXAMPLE 40 cis-3-Cyclohexyloxy-6-(2-quinolyl)methoxy-4-chromanyl N,N-Dimethylglycinate

The cis-title product of Example 5 (0.22 mmol) is dissolved in CH$_2$Cl$_2$ (3 ml). 4-(Dimethylamino)pyridine (0.043 g, 0.35 mmol), N,N-dimethylglycine hydrochloride (0.038 g, 0.26 mmol) and dicyclohexylcarbodiimide (0.050 g, 0.26 mmol) are then added in the listed sequence and the mixture is stirred for 18 hours. The reaction mixture is quenched with an equal volume of water and by-product dicyclohexyl urea removed by filtration. The organic layer in the filtrate is separated, washed with saturated NaHCO$_3$, water and brine, dried over Na$_2$SO$_4$ and stripped to yield present title product.

The corresponding glycinate esters are obtained from the trans-title product of Example 11, as well as from the title products of Examples 7, 11, 13, 14 and 16, by the same method.

EXAMPLE 41 cis-3-Cyclohexyloxy-6-(2-quinolyl)methoxy-4-chromanyl N,N-Dimethylglycinate Dihydrochloride To the title product of the preceding Example (0.10 g, 0.19 mmol) dissolved in 5 ml absolute ethanol is added 0.475 ml (0.475 mmol) of 1N HCl and the mixture stirred for several minutes, then stripped to dryness to yield present title product.

EXAMPLE 42 trans-2-Butyl-1,2,3,4-tetrahydro-7-(2-quinolyl) methoxy-1-naphthyl 4-Piperidinobutyrate Dihydrochloride To a 0° C. solution of 935 mg (4.52 mmol) of 4-piperidinobutyric acid hydrochloride, 733 mg (6.01 mmol) 4-(N,N-dimethylamino)pyridine and 1.36 g (3.77 mmol) of the trans-title product of Example 11 in 7.5 ml CH$_2$Cl$_2$ is added 852 mg (4.14 mmol) dicyclohexylcarbodiimide. The resultant reaction mixture is stirred 15 hours at 25° C., then filtered and the filtrate evaporated to dryness. The resulting residue is dissolved in 100 ml ethanol. 1N Hydrochloric acid (7.54 ml) is added, and the reaction concentrated to dryness on a rotating evaporator to yield present title product.

EXAMPLE 43

3,4-Dihydro-7-(2-quinolyl)methoxy-1 (2H)-naphthalenone

By the method of Example 10, 5.00 g (30.9 mmol) of 7-hydroxy-3,4-dihydro-1 (2H)naphthalenone and 9.91 g (46.3 mmol) of 2-chloromethylquinoline hydrochloride gave 3.5 g (37%) of the title compound.

MS (m/e) 303 (M$^+$), 286, 274, 142, and 115.

$^1$H-NMR(CDCl$_3$, 300 MHz)delta(ppm): 2.08 (m, 2H), 2.60 (t, J=7 Hz, CH$_2$), 2.87 (t, J=6 Hz, CH$_2$), 5.39 (s, OCH$_2$), 7.16 (d, J=2 Hz, ArH), 7.52 (dd, J=8, 8 Hz, ArH), 7.6–7.75 (m, 4ArH), 7.79 (d, J=8 Hz, ArH), 8.07 (d, J=8 Hz, ArH) and 8.16 (d, J=8 Hz, ArH).

EXAMPLE 44

By the method of Example 22, using the appropriate aldehyde as reactant, the title product of the preceding Example is converted to:

2 (4H)-Hexylidene-7-(2-quinolyl)methoxy-1 (3H)-naphthalenone;
2(4H)-Cyclopentylmethylene-7-(2-quinolyl)methoxy-1 (3H)-naphthalenone; and
2 (4H)-(2,2-Difluorobutylidene)-7-(2-quinolyl)methoxy-1 (3H)-naphthalenone.

EXAMPLE 45

By the method of Example 23, the products of the preceding Example are converted to:

3,4-Dihydro-2-hexyl-7-(2-quinolyl)methoxy-1 (2H)-naphthalenone;
3,4-Dihydro-2-cyclopentylmethyl-7-(2-quinolyl)methoxy-1 (2H)-naphthalenone; and
3,4-Dihydro-2-(2,2-difluorobutyl)-7-(2-quinolyl)methoxy-1 (2H)-naphthalenone.

EXAMPLE 46

By the method of Example 5, the products of the preceding Example are converted to:

cis- and trans- 1,2,3,4-Tetrahydro-2-hexyl-7-(2-quinolyl)methoxy-1-naphthol;
cis- and trans-1,2,3,4-Tetrahydro-2-cyclopentylmethyl-7-(2-quinolyl)methoxy-1-naphthol; and
cis- and trans-1,2,3,4-Tetrahydro-2-(2,2-difluorobutyl)-7-(2-quinolyl)methoxy-1-naphthol.

EXAMPLE 47

2-Butylidene-6-methoxy-1-indanone

To a 0° C. mixture of 9.66 g (59.6 mmol) of 6-methoxy-1-indanone and 4.29 g (59.6 mmol) of butyr-aldehyde in 10 ml ethanol is added 9.66 ml of a 4% KOH in ethanol solution. The reaction is stirred 1 hour and then added to 300 ml water and the pH of the quench adjusted to 2 with 1N hydrochloric acid. The resultant mixture is extracted with 3×300 ml ether, and the extracts combined, dried over MgSO$_4$, evaporated and the residue triturated with ether to yield present title compound.

EXAMPLE 48

2-Butyl-6-methoxy-1-indanone

By the method of Example 18, the title product of the preceding Example is converted to present title compound.

EXAMPLE 49

2-Butyl-6-hydroxy-1-indanone

By the method of Preparation 3, below, 8.00 g (31.7 mmol) of the title product of the preceding Example is converted to present title compound.

EXAMPLE 50

2-Butyl-6-(2-quinolyl)methoxy-1-indanone

By the method of Example 10, 14.7 mmol of the title product of the preceding Example and 4.80 g (22.4 mmol) of 2-chloromethylquinoline hydrochloride are converted to present title compound. Substituting a molar equivalent of 2-, 3- or 4-picolyl chloride hydrochloride for the 2-chloromethylquinoline hydrochloride of this process produces the corresponding 2-butyl-6-(2-, 3- and 4-pyridyl)methoxy-1-indanones, respectively.

EXAMPLE 51 cis- and trans-2-Butyl-6-(2-quinolyl)methoxy-1-indanol

By the method of Example 5, the title product of the preceding Example is converted to present title products.

EXAMPLE 52

3-Pentylidene-6-methoxy-1-(p-toluenesulfonyl)-2,3-dihydro-4 (1H)-quinolinone By the method of Example 22, 25.0 g (75.5 mmol) of 6-methoxy-1-toluenesulfonyl-2,3-dihydro-4 (1H)-quinolinone (*J. Am. Chem. Soc.,* Vol. 71, p. 1901, 1949) and 9.7 g (113 mmol) of pentanal are converted to present title product.

EXAMPLE 53

6-Methoxy-1-(p-toluenesulfonyl)-3-pentyl-2,3-dihydro-4 (1H)-quinolinone

By the method of Example 23, the product of the preceding Example is converted to present title product.

EXAMPLE 54

6-Hydroxy-3-pentyl-2,3-dihydro-4 (1H)-quinoline

A mixture of 10 g of the title product of the preceding Example in 35 ml acetic acid and 35 ml of concentrated HBr is refluxed for 8 hours, then added to ice and water to precipitate present title product.

EXAMPLE 55

6-Hydroxy-3-pentyl-1-(p-toluenesulfonyl)-2,3-dihydro-4 (1H)-quinolone

To a solution of 8.66 mmol of title product of the preceding Example in 13 ml pyridine is added gradually 1.65 g (8.66 mmol) of p-toluenesulfonyl chloride. The reaction is stirred 1 hour, then added to 200 ml 1N HCl and extracted with ethyl acetate. The organic layer is washed with fresh 1N HCl and then saturated NaCl, dried over MgSO$_4$ and stripped to yield present title product.

EXAMPLE 56

By the method of Example 1 or 10, the title product of the preceding Example is reacted with the appropriate heteroarylmethyl chloride to produce the corresponding 6-(2-quinolyl, 2-pyridyl, 3-pyridyl, 4-pyridyl, 2-quinoxalinyl, 2-pyrimidinyl, 6-fluoro-2-quinolyl, 5-fluoro-2-benzothiazolyl and 1-phthalazinyl)methoxy derivatives. These in turn are hydrolyzed (1 g) by refluxing for 8–9 hours in a mixture of 7.5 ml of acetic acid and 4 ml concentrated HCl, followed by dilution with an equal volume of water, adjustment of the pH to 8.0 with 6N NaOH and extraction into $CH_2Cl_2$. The organic layer is dried over $MgSO_4$ and stripped to yield the desired ketone products:

2,3-Dihydro-3-pentyl-6-(2-quinolyl)methoxy-4 (1H)-quinolone;
2,3-Dihydro-3-pentyl-6-(2-pyridyl)methoxy-4 (1H)-quinolone;
2,3-Dihydro-3-pentyl-6-(3-pyridyl)methoxy-4 (11H)-quinolone;
2,3-Dihydro-3-pentyl-6-(4-pyridyl)methoxy-4 (1H)-quinolone;
2,3-Dihydro-3-pentyl-6-(2-quinoxalinyl)methoxy-4 (1H)-quinolone;
2,3-Dihydro-3-pentyl-6-(2-pyrimidinyl)methoxy-4 (1H)-quinolone;
2,3-Dihydro-3-pentyl-6-(6-fluoro-2-quinolyl)methoxy-4 (1H)-quinolone;
2,3-Dihydro-3-pentyl-6-(5-fluoro-2-benzothiazolyl) methoxy-4 (1H)-quinolone; and
2,3-Dihydro-3-pentyl-6-(1-phthalazinyl)methoxy-4 (1H)-quinolone.

EXAMPLE 57

By the method of Example 5, the products of the preceding Example are converted to the corresponding cis- and trans-1,2,3,4-tetrahydro-3-pentyl-6-(substituted)methoxy-4-quinolols.

EXAMPLE 58

3-Butyl-6-(2-quinolyl)methoxythiochroman-4-one

By the sequential steps of Examples 8 to 10, 7-methoxythiochroman-4-one is converted to present title product.

EXAMPLE 59 cis- and trans-3-Butyl-6-(2-quinolyl) methoxythiochroman-4-one-1-oxide

To a −5° to 0° C. solution of 30 mmol of title product of the preceding Example in 100 ml $CH_2Cl_2$ is slowly added 31 mmol of m-chloroperbenzoic acid. The mixture is stirred until a starch-KI test paper is negative (a few hours), then quenched into 100 ml $H_2O$. The organic layer is separated, washed with saturated $NaHCO_3$, dried over $MgSO_4$ and stripped to yield title products.

By using 70 mmol of m-chloroperbenzoic acid and extending the reaction time to 16 hours at room temperature, one obtains the corresponding sulfone (1,1-dioxide).

EXAMPLE 60

By the method of Example 5, the title products of the preceding three Examples are converted to the corresponding cis- and trans-thiochroman-4-ols.

EXAMPLE 61

7,8-Dihydro-7-methyl-3-(2-quinolyl)methoxy-5 (6H)-quinolone

By the method of Example 1, 7,8-dihydro-3-hydroxy-7-methyl-5 (6H)-quinolone and 2-chloromethylquinoline were converted to present title product in 67% yield, m.p. 141–144° C.

MS (m/e) calculated: 318.1365; found: 318.1325.

By using 70 mmol of m-chloroperbenzoic acid and extending the reaction time to 16 hours at room temperature, one obtains the corresponding sulfone (1,1-dioxide).

EXAMPLE 60

By the method of Example 5, the title products of the preceding three Examples are converted to the corresponding cis- and trans-thiochroman-4-ols.

EXAMPLE 61

7,8-Dihydro-7-methyl-3-(2-quinolyl)methoxy-5 (6H)-quinolone

By the method of Example 1, 7,8-dihydro-3-hydroxy-7-methyl-5 (6H)-quinolone and 2-chloromethylquinoline were converted to present title product in 67% yield, m.p. 141–144° C.

MS (m/e) calculated: 318.1365; found: 318.1325.

Preparation 1

4-(2-Cyanoethoxy)anisole

4-Methoxyphenol (248 g), KOH (5.6 g) and acrylo-nitrile (397 ml) were dissolved in 1 liter of t-butanol and heated with stirring at 75° C. for 5 hours. The mixture was then cooled to room temperature and stripped in vacuo to solid residue, which was repulped in ether and insolubles recovered by filtration. The latter were taken up in 2 liters of ethyl acetate, washed in sequence with 1 liter each of $H_2O$, saturated $NaHCO_3$ and saturated NaCl, dried over $MgSO_4$ and restripped to yield purified title product, 199.4 g, m.p. 62–64° C.

Preparation 2

6-Methoxy-4-chromanone

The title product of the preceding Example (199 g) was combined with 240 ml $H_2O$ and 480 ml of concentrated HCl and heated at reflux overnight. The reaction mixture was cooled to room temperature and solids recovered by filtration. The latter were taken up in 2 liters of ethyl acetate, washed with 200 ml of $H_2O$, dried over $MgSO_4$ and stripped in vacuo to yield intermediate 3-(4-methoxyphenoxy) propionic acid, 195 g, m.p. 105–107° C. The latter was added to 600 ml of hot, stirred polyphosphoric acid maintained at 75° C. and the mixture stirred for 2 hours. The temperature rose to a maximum of 89° C. over the first one-half hour, then fell to the 75° C. bath temperature. The reaction mixture was quenched into 3.2 liters of ice and water and extracted with 1.2 liters of ethyl acetate. The organic extract was in sequence with 600 ml each of $H_2O$, saturated $NaHCO_3$ and saturated NaCl, dried over $MgSO_4$ and stripped to 180 g of solids which were taken up in 400 ml $CH_2Cl_2$, treated with activated carbon and restripped to a like quantity of solids. The latter were recrystallized from isopropyl ether to yield purified title product, 120 g, m.p. 46–48° C., identical with the commercial product.

Preparation 3

6-Hydroxy-4-chromanone

A solution of 36 g of the product of the preceding Preparation in 290 ml of acetic acid and 290 ml of 48% hydrobromic acid was heated at reflux for 3 hours. The reaction was cooled and stripped in vacuo to crude product which was diluted with water (6 liters), cooled to 0–5° C. and title product recovered by filtration, 25.7 g (80%), m.p. 133–136° C. Optionally, the product is further purified by chromatography on silica gel using ethyl acetate/hexane as eluant.

Preparation 4

6-Benzyloxy-4-chromanone

A mixture of 25 g of the product of the preceding Preparation, 26.5 g of benzyl bromide and 28 g of potassium carbonate in 150 ml of acetone was heated at reflux overnight. The reaction was cooled and filtered to remove potassium carbonate. The filtrate was evaporated and the residue was dissolved in ethyl acetate and washed with water. The ethyl acetate layer was dried over sodium sulfate and evaporated in vacuo to obtain the crude product, which was purified by recrystallization from methylene chloride/hexane to give 29 g of title product, m.p. 107–108° C.

$^1$H-NMR(acetone-$d_6$)delta(ppm): 2.7 (t, 2H), 4.4 (t, 2H), 5.08 (s, 2H), 7.2–7.5 (m, 3H).

Preparation 5

3-Hydroxymethylene-6-benzyloxy-4-chromanone

To a solution of 172.5 g of the product of the preceding Preparation in 1.7 liters of toluene containing 168 ml of ethyl formate and 3.5 ml of ethanol was added, in portions, 66 g of 50% sodium hydride. The reaction was allowed to stir at room temperature for 1 hour, then poured into 1.5 liters of ice and $H_2O$, and acidified to pH 4 with dilute hydrochloric acid. The aqueous layer was extracted with several portions of ethyl acetate. The organic layers were combined, dried over sodium sulfate and evaporated in vacuo to give the crude product which was triturated with hexane to remove hydride oil. The resultant product crystallized on standing, m.p. 82–85° C.

Preparation 6

3-Diazo-6-benzyloxy-4-chromanone

To a −10° C. solution of 35.3 g of title product of the preceding Preparation in 250 ml of dichloromethane containing 25.2 g of triethylamine was added dropwise a solution of 24.4 g of tosyl azide in 100 ml of dichloromethane. After complete addition, the reaction was allowed to warm to room temperature and stirred overnight. The reaction mixture was washed with water, dried over sodium sulfate and evaporated in vacuo to give the crude product, which was purified by column chromatography on silica gel eluting with dichloromethane to give 21 g of product, m.p. 100–103° C.

$^1$H-NMR(CDCl$_3$)delta(ppm): 5.02 (d, J=4, 2H), 6.7–7.5 (m, 10H).

Preparation 7

4-(4-Methoxyphenoxy)butyric Acid

4-Methoxyphenol was added to a solution of NaOC$_2$H$_5$ made by dissolving 2.3 g of Na in 50 ml ethanol. After 5 minutes, gamma-butyrolactone was added and the mixture heated at reflux overnight. Ethanol was distilled off and the residue heated at 155° C. overnight, then cooled, diluted with water and acidified to pH 3 with dilute hydrochloric acid. The product was collected by filtration, 19.5 g, m.p. 103–104° C.

Preparation 8

3,4-Dihydro-7-methoxy-1-benzoxepin-5 (2H)-one

The product of the preceding Preparation, 34 g, was dissolved in 300 ml of polyphosphoric acid and heated at 100° C. for 1 hour. The reaction was cooled, poured into water and extracted with ether to give the crude product. It was purified by distillation, b.p. 100° C./0.5 mm.

Preparation 9

3,4-Dihydro-7-hydroxy-1-benzoxepin-5 (2H)-one

A mixture of 19.23 g of the product of the preceding Preparation, 95 ml of 48% hydrobromic acid and 95 ml of acetic acid was heated at reflux for 4 hours. The reaction was cooled and evaporated in vacuo to afford the crude product, which was purified by column chromatography on silica gel, eluting with dichloromethane to give 8.3 g of product, m.p. 116–120° C.

$^1$H-NMR(CDCl$_3$)delta(ppm): 2.0–2.45 (m, 2H), 2.95 (t, J=7, 2H), 4.20 (t, J=7, 2H), 6.8–7.1 (m, 3H), 7.4 (s, 1H).

Preparation 10

7-Benzyloxy-3,4-dihydro-1-benzoxepin-5 (2H)-one

A mixture of 6.5 g of the product of the preceding Preparation, 4.3 ml of benzyl bromide, 6.3 g of potassium carbonate and 40 ml of acetone was heated with stirring at reflux overnight. The reaction was cooled and filtered to remove inorganics. The filtrate was evaporated in vacuo, and the residue dissolved in ethyl acetate and washed with water. The ethyl acetate layer was dried over sodium sulfate and evaporated in vacuo to give the crude product which was purified by recrystallization from isopropyl ether to give 8.4 g of title product, m.p. 62–63° C.

Preparation 11

7-Benzyloxy-4-bromo-3,4-dihydro-1-benzoxepin-5 (2H)-one

To a solution of 6.3 g of the title product of the preceding Preparation in 25 ml of acetic acid was added a solution of 3.76 g of bromine in 25 ml of acetic acid. The reaction was stirred for 3 minutes and the volatiles evaporated in vacuo to a residue which was dissolved in ethyl acetate and washed with water. The ethyl acetate layer was dried and evaporated to give 8.2 g of product which was used without purification in the next step.

Preparation 12

3-Bromo-6-methoxy-4-quinolone

To a solution of 6-methoxy-4-chromanone (35 g) in ethyl ether (1.6 liters) at 5–10° C. was added dropwise over 30 minutes 10.6 ml of bromine. The mixture was stirred at 5–10° C. for 30 minutes and then allowed to warm to room temperature. After 2 hours tlc (CH$_2$Cl$_2$) indicated formation of less polar products and only a trace of starting material remaining. The reaction mixture was washed with water (1 liter), saturated NaHCO$_3$ (500 ml), and brine (500 ml), dried over MgSO$_4$, and concentrated in vacuo to a yellow solid. The crude product was purified by silica gel flash column chromatography on 2.4 Kg fine silica gel, eluting with a gradient system consisting of 3:1 hexanes/dichloromethane followed by 2:1 hexanes/dichloromethane and finally 30% hexanes/dichloromethane. This afforded title product as a yellow solid in 80% yield.

Preparation 13

1-Amino-5-methylcyclohex-1-en-3-one

5-Methyl-1,3-cyclohexanedione (40 g, 0.32 mol) was dissolved in 500 ml of benzene at 70° C. The solution was heated at reflux for 2 hours, during which $NH_3$ was bubbled through the reaction mixture and formed $H_2O$ was collected in a Dean-Stark trap. The mixture was then cooled to 0° C. and title product recovered by filtration, 39.8 g, m.p. 165–169° C.

$^1$H-NMR(DMSO-$d_6$)delta(ppm): 0.98 (s, 3H), 1.6–1.88 (2H), 2.14–2.38 (2H), 3.14–3.6 (1H), 4.93 (s, 1H), 6.2–7.2 (m, 2H).

Preparation 14

7,8-Dihydro-7-methyl-3-nitro-5 (6H)-quinolone

Sodium nitromalonaldehyde (*Org. Synth. Coll.*, vol. 4, p. 844; 42.4 g, 0.269 mol) was dissolved in 200 ml of dimethylformamide and the resulting solution dried over 4A-type molecular sieves, recovered by filtration with 100 ml of the same solvent for wash. To the combined filtrate and wash was added pyridine (91 ml, 89 g, 1.13 mol) and the mixture cooled to −5° C. Tosyl chloride (53 g, 0.277 mol) in 200 ml of dimethylformamide was added dropwise, maintaining a temperature of −5° to −8° C., and the reaction mixture allowed to warm to room temperature. The title product of the preceding Preparation (33.6 g, 0.270 mol), dissolved by warming in 200 ml of dimethylformamide and added in a steady stream to the reaction mixture, which was then stirred for 18 hours at room temperature, then poured into 2 liters of ice and water and extracted 2×1 liter of ethyl acetate. The organic layers were combined, dried over $MgSO_4$ and stripped to yield present title product, 33 g (61%), m.p. 64–67° C.

Preparation 15

3-Amino-7,8-dihydro-7-methyl-5 (6H)-quinolone

Title product of the preceding Preparation (27 g) was placed in a 250 ml Parr bottle with 830 ml absolute ethanol and 9.0 g 10% Pd/C. This was then agitated on a Parr apparatus under 50 psia $H_2$ for 2 hours at room temperature. The catalyst was recovered by filtration over diatomaceous earth and the filtrate was concentrated to dryness. The resulting brown solid was flash chromatographed by first dissolving in $CH_3OH$, adding 50 ml dry 32–63 micron silica gel and concentrating to dryness. The resulting material was then charged dry onto a 30 cm×15 cm column of fresh silica gel which had been wet packed with 1% triethylamine in 19:1 $CH_2Cl_2$:isopropanol. The column was eluted with the same solvent system. Middle product-containing fractions were combined and stripped to yield present title product, MS (m/e) calculated: 176.0950, found: 176.0944; tlc (19:1 $CH_2Cl_2$:$C_2H_5OH$) Rf 0.32.

Preparation 16

7,8-Dihydro-7-methyl-5 (6H)-quinolone6-diazonium Hexafluorophosphate

At room temperature, title product of the preceding Preparation (15.26 g) was placed in a 500 ml 3-necked flask equipped with a mechanical stirrer, dropping funnel and venting line placed up the back of the fume hood. Then 6.93 ml glacial acetic acid was added. 159 Ml of 3.48N HCl was then added all at once whereupon the reaction mixture became a clear deep red solution. The latter was then cooled to 0° C. at which time some solid precipitated out of solution. To this slurry, still at 0° C., was then added 5.98 g $NaNO_2$ in 35 ml $H_2O$, dropwise over 5–10 minutes, and the resulting mixture stirred at 0° C. for 30 minutes. Still maintaining 0° C., 15.24 ml $HPF_6$ (60 weight % in $H_2O$) was added over 5 minutes. A light brown precipitate formed immediately. Vigorous stirring was continued for 10–15 minutes after addition was complete. The resulting solid was filtered, washed with 2×25 ml cold $H_2O$, 2×25 ml ether and then dried under high vacuum overnight over $P_2O_5$ to yield 25.62 g (89%) of present title product, m.p. 175–176.5° C.

Preparation 17

7,8-Dihydro-3-hydroxy-7-methyl-5 (6H)-quinolone

Title product of the preceding Example (25.62 g) was added in 0.5 g portions to 500 ml of boiling 5% $H_2SO_4$ over a time period (2.5 hours in this instance) which avoided excessive foaming due to $N_2$ evolution. The reaction mixture was heated at reflux for an additional 40 minutes, then cooled to 0° C. and adjusted to pH 7 with 6N NaOH (160 ml required in this instance). The reaction mixture was extracted 3×250 ml ethyl acetate. In the first extraction, the emulsion was broken by filtration over diatomaceous earth. The organic extracts were combined, dried over $MgSO_4$, stripped to solids, and the residue dissolved in $CH_3OH$, slurried with silica gel, stripped and flash chromatographed as in the preceding Example, using 19:1 $CH_2Cl_2$:isopropanol as eluant to yield present title product, 9.2 g (67%), m.p. 210.5–212° C.

Preparation 18

3-Benzyloxy-7,8-dihydro-7-methyl-5 (6H)-quinolone

By the method of Preparation 4, the product of the preceding Preparation was converted to present title product in 78% yield, m.p. 80.5–81.5° C. MS (m/e) calculated: 267.1259, found: 267.1261.

Preparation 19

2-Chloromethylquinoxaline

2-Methylquinoxaline (8.94 g) was combined with 50 ml $CCl_4$ and 6.5 g $Na_2CO_3$ in a 125 ml beaker. This was heated to 68° C. and then $Cl_2$ was introduced via an inverted funnel so that the $Cl_2$ was bubbled very slowly. This was continued for 1 hour and then the reaction mixture was cooled to 20° C. in an ice bath and partitioned between ether and saturated $NaHCO_3$ solution. The ether was separated, dried over $MgSO_4$, and concentrated to dryness. The residue was immediately flashed down a column packed with 20 cm of 32–63 micron silica gel (the column having a diameter of 8 cm) using 1:1 ether:hexane as eluant. After a 1 liter forerun, 250 ml fractions were collected. Fractions 3–5 were combined and concentrated to yield 2.58 g (23%) of title product as a yellow solid; tlc (3:7 ethyl acetate:$CH_2Cl_2$) Rf 0.65.

$^1$H-NMR(CDCl$_3$)delta(ppm): 4.86 (s, 2H), 7.74–7.78 (m, 2H), 8.02–8.16 (m, 2H), 9.0 (m, 1H).

Preparation 20

2-Bromo-3,4-dihydro-7-methoxy-1 (2H)-naphthalenone

To a 10° C. solution of 25 g (0.142 mol) of 7-methoxy-3,4-dihydro-1 (2H)-naphthalenone in 1 liter ether was added dropwise (maintaining reaction temperature at about 10° C.) 37.9 g (0.237 mol) of bromine. The reaction solution was concentrated on a rotating evaporator and the residue crystallized from ether to give 31.6 g (87%) of present title compound, m.p. 79–80° C.

MS (m/e) 256 and 254 (M$^+$), 174, 173, 148, 131, 120, 115 and 103. Ir (CHCl$_3$) 1680, 1610 cm$^{-1}$.

$^1$H-NMR(CDCl$_3$)delta(ppm): 2.2–2.7 (m, 2H), 2.9–3.5 (m, 2H), 3.95 (s, OCH$_3$), 4.78 (t, J=4 Hz, CHBr), 7.0–7.4 (m, 2ArH) and 7.58 (bs, ArH).

Analysis calculated for C$_{11}$H$_{11}$BrO$_2$.H$_2$O: C, 50.89; H, 4.46%. Found: C, 50.71; H, 4.36%.

Preparation 21

6-Benzyloxy-3-methylene-4-chromanone

A solution of 9.2 g of 6-benzyloxy-4-chromanone, dimethylamine hydrochloride and 1.3 g of paraformaldehyde in 100 ml of acetic acid was heated on a steam bath for 5 hours. The volatiles were evaporated in vacuo and the residue was purified on silica gel, eluting with CH$_2$Cl$_2$, to give 3.7 g of product, Rf (CH$_2$Cl$_2$)=0.5.

$^1$H-NMR(CDCl$_3$)delta(ppm): 4.95 (s, 2H), 5.05 (s, 2H), 5.55 (s, 1H), 6.30 (s, 1H), 6.80–7.60 (m, 8H).

Preparation 22

3-Bromo-2-(bromomethyl)-6-methyl pyridine and 3-Bromo-6-(bromomethyl)-2-methyl pyridine To a 25 ml round bottomed flask equipped with a stir bar and condenser, under an inert atmosphere, were added 1.4 g (7.35 mmol) of 3-bromo-2,6-lutidine, 1.21 g (6.77 mmol) of N-bromosuccinimide, 4.5 ml of carbon tetrachloride, and 10 mg (0.04 mmol) of benzoyl peroxide. The resulting mixture was refluxed overnight. Tlc at this point indicated that there still was starting material present, so 0.7 g (3.9 mmol) of N-bromosuccinimide was added and the reaction mixture refluxed for an additional 4 hours. The precipitate was filtered off and washed 2×50 ml CCl$_4$ (hot). The filtrate was concentrated to an oil and the crude product was then purified by flash chromatography on 200 g silica gel with 3:1 hexane:CH$_2$Cl$_2$ as eluant to yield the two title compounds, 218 mg (11%) yield of the 2-(bromomethyl) derivative and 285 mg (14%) yield of the 6-(bromomethyl) derivative, tlc (3:1 hexane:CH$_2$Cl$_2$) Rf 0.07 and 0.13, respectively.

2-(bromomethyl) derivative.

$^1$H-NMR(DMSO-d$_6$)delta(ppm): 7.99 (d, J=7.8 Hz, 1H), 7.19 (d, J=7.8 Hz, 1H), 4.71 (s, 2H), 2.46 (s, 3H).

6-(bromomethyl) derivative.

$^1$H-NMR(DMSO-d$_6$)delta(ppm): 8.00 (d, J=7.8 Hz, 1H), 7.32 (d, J=7.8 Hz, 1H), 4.63 (s, 2Hz), 2.56 (s, 3H).

What is claimed is:

1. A method of inhibiting 5-lipoxygenase and/or blocking leukotriene D4 receptors in a mammal in need of such inhibition and/or blocking which comprises administering to said mammal a 5-lipoxygenase inhibiting and/or leukotriene D4 receptor blocking amount of a racemic or optically active compound having the structural formula wherein
  n is 0 or 1;
  X is CH$_2$;
  X$^1$ is CH$_2$;
  Y and Y$^1$ taken together form =O, or Y is hydrogen and Y$^1$ is hydroxy;
  Z is CH$_2$;
  Z$^1$ is CH;
  R is 2-, 3- or 4-quinolyl, said group being mono- or disubstituted on carbon with the same or different substituents which are bromo, chloro, fluoro, (C$_1$–C$_4$) alkyl, trifluoromethyl, hydroxy, hydroxymethyl or (C$_1$–C$_4$)alkoxy, or substituted on adjacent carbons with trimethylene, tetramethylene, —CH$_2$—O—CH$_2$, or —O—CH$_2$—O; and
  R$^1$ is (C$_7$–C$_{10}$)bicycloalkyl, (C$_4$–C$_{10}$)cycloalkylalkyl, (C$_8$–C$_{11}$)bicycloalkylalkyl, or one said groups mono- or disubstituted with the same or different groups which are fluoro, (C$_1$–C$_4$)alkyl, (C$_1$–C$_4$)alkoxy, carboxy or -carbonyl;
a pharmaceutically acceptable acid addition salt thereof; or
a pharmaceutically acceptable cationic salt when the compound contains a carboxy group wherein the mammal is a human suffering from a condition selected from the group consisting of asthma, arthritis, psoriasis, and gastrointestinal distress, and said compound is administered to prevent or relieve the symptoms of said condition.

2. A method of claim 1 wherein Y and Y$^1$ are taken together and form a carbonyl group.

3. A method of claim 1 wherein the mammal is suffering from arthritis.

4. A method of claim 1 wherein the mammal is a human suffering from psoriasis.

5. A method of claim 1 wherein the mammal is suffering from gastrointestinal distress.

6. A method of inhibiting 5-lipoxygenase and/or blocking leukotriene D4 receptors in a mammal in need of such inhibition and/or blocking which comprises administering to said mammal a 5-lipoxygenase inhibiting and/or leukotriene D4 receptor blocking amount of a racemic or optically active compound having the structural formula wherein
  n is 0 or 1;
  X is CH$_2$;
  X$^1$ is CH$_2$;
  Y and Y$^1$ taken together form =O, or Y is hydrogen and Y$^1$ is hydroxy;

Z is $CH_2$;

$Z^1$ is CH;

R is 2-quinolyl; said group being mono- or disubstituted on carbon with the same or different substituents which are bromo, chloro, fluoro, $(C_1-C_4)$alkyl, trifluoromethyl, hydroxy, hydroxymethyl or $(C_1-C_4)$alkoxy, or substituted on adjacent carbons with trimethylene, tetramethylene, —$CH_2$—O—$CH_2$—, or —O—$CH_2$—O; and $R^1$ is $(C_7-C_{10})$bicycloalkyl, $(C_4-C_{10})$cycloalkylalkyl, $(C_8-C_{11})$bicycloalkylalkyl, or one of said groups mono- or disubstituted with the same or different group which are fluoro, $(C_1-C_4)$alkyl, $(C_1-C_4)$alkoxy, carboxy, or carbonyl;

a pharmaceutically acceptable acid addition salt thereof; or a pharmaceutically acceptable cationic salt when the compound contains a carboxy group wherein the mammal is a human suffering from a condition selected from the group consisting of asthma, arthritis, psoriasis, and gastrointestinal distress, and said compound is administered to prevent or relieve the symptoms of said condition.

7. A method of claim 6 wherein $Y^1$ is hydroxy.

8. A method of claim 6 wherein the mammal is suffering from arthritis.

9. A method of claim 6 wherein the mammal is a human suffering from psoriasis.

10. A method of claim 6 wherein the mammal is suffering from gastrointestinal distress.

11. A method of claim 1 wherein said condition is asthma.

12. A method of claim 6 wherein said condition is asthma.

* * * * *